United States Patent [19]
Liu et al.

[11] Patent Number: 6,023,637
[45] Date of Patent: Feb. 8, 2000

[54] METHOD AND APPARATUS FOR THERMAL RADIATION IMAGING

[76] Inventors: Zhong Qi Liu; Chen Wang, both of Dong San Men Haidian Stadium, Beijing 100080, China

[21] Appl. No.: 08/964,245

[22] Filed: Nov. 4, 1997

Related U.S. Application Data

[60] Provisional application No. 60/042,214, Mar. 31, 1997.

[51] Int. Cl.$^7$ .................................................. A61B 5/00
[52] U.S. Cl. ........................... 600/474; 348/77; 348/164; 128/922; 382/128
[58] Field of Search .................................. 600/407, 410, 600/412, 473, 474, 549; 348/77, 164; 382/274, 128; 250/330, 338.1, 339.11, 339.02; 128/920, 922

[56] References Cited

U.S. PATENT DOCUMENTS

| | | | |
|---|---|---|---|
| 3,862,423 | 1/1975 | Kutas et al. | 250/347 |
| 3,909,521 | 9/1975 | Hunt et al. | 178/7.2 |
| 4,170,987 | 10/1979 | Anselmo et al. | 128/665 |
| 4,407,292 | 10/1983 | Edrich | 128/653 |
| 4,428,382 | 1/1984 | Walsall et al. | 128/736 |
| 4,515,165 | 5/1985 | Carroll | 128/664 |
| 4,548,212 | 10/1985 | Leung | 128/736 |
| 4,641,659 | 2/1987 | Sepponen | 128/653 |
| 5,034,794 | 7/1991 | Murotani | 357/30 |
| 5,056,525 | 10/1991 | Hafezi | 128/664 |
| 5,088,493 | 2/1992 | Giannini et al. | 128/633 |
| 5,148,022 | 9/1992 | Kawaguchi et al. | 250/341 |
| 5,213,105 | 5/1993 | Gratton et al. | 128/664 |
| 5,305,579 | 4/1994 | Kaneko et al. | 128/665 |
| 5,474,085 | 12/1995 | Hurnik et al. | 128/774 |
| 5,497,770 | 3/1996 | Morcos et al. | 128/633 |
| 5,594,248 | 1/1997 | Tanaka | 250/332 |
| 5,692,511 | 12/1997 | Grable | 128/664 |

OTHER PUBLICATIONS

PCT International Search Report for US 98/05996, dated Jul. 20, 1998.

Kassen, et al.; "Differential–thermography a method for the early diagnosis of mammary carcinomas by on–line image processing," IEEE Transactions on Nuclear Science, vol. 30, No. 5, Oct. 1983, New York, US, pp. 3989–3992, XP002070590.

Van Deursen, et al., "Microprocessor system for control and analysis of thermographic images," Medical & Biological Engineering & Computing, vol. 23, Nov. 1985, Stevenage, GB, pp. 589–592, XP002070591.

US 4 849 885 A (Stillwagon et al.) Jul. 18, 1989.

Shimmins, et al., "The digitization and analysis of thermographcic images," Physics in Medicine and Biology, vol. 22, No. 1, Jan., 1977, London, GB, pp. 95–97, XP002070592.

PCT International Search Report for PCT/IB98/01320, dated Dec. 17, 1998.

*Primary Examiner*—George Manuel
*Assistant Examiner*—Shawna J. Shaw
*Attorney, Agent, or Firm*—Arnold, White & Durkee

[57] ABSTRACT

A method and apparatus for thermal imaging is disclosed which enables a clinician to obtain visual images reflecting metabolic activity within a patient's body. A scanning system is configured to scan an area on the patient's body to obtain infrared intensity data. The data is digitized and processed prior to being displayed. The data processing includes a "slicing" function in which infrared intensity values are assigned color values in accordance with an output window. By redefining the mapping of the output window to the color spectrum, the data can be manipulated such that the visual display reflects metabolic activity within the patient's body under the scanning area.

10 Claims, 19 Drawing Sheets

(2 of 19 Drawing Sheet(s) Filed in Color)

METHOD AND APPARATUS FOR THERMAL RADIATION IMAGING

PRIOR APPLICATIONS

This application claims the benefit of priority of prior provisional U.S. patent application Ser. No. 60/042,214 filed on Mar. 31, 1997.

FIELD OF THE INVENTION

This invention relates generally to the field of thermography, and more particularly to a method and apparatus for thermographic imaging.

BACKGROUND OF THE INVENTION

Those of ordinary skill in the art will appreciate that living cells within a biological body are constantly undergoing metabolic activities. These biochemical and physical metabolic processes generate heat. Certain cells, like cancer cells, have been shown to have a high metabolic rate, thus producing a high amount of heat relative to other cells. On the other hand, bones have a lower metabolic rate and generate lower amount of heat. Aging or lifeless cells do not emit heat, but rather absorb heat.

Thermal radiation resulting from the metabolic generation of heat emanates from the human body. The patterns of such thermal emissions are affected by the activities of the tissues, organs and vessels inside the body. The amount of radiation can reflect the metabolic rate of the human body.

The application of clinical thermography, a technology involving the measurement and displaying of self-emanating radiation to reveal thermal changes on the surface of the human body, began possibly as early as the 1930's. Over the years, thermographic technology has been extensively tested and examined in clinical studies.

One example of a prior art thermographic scanning system is U.S. Pat. No. 3,909,521 to Hunt et al., entitled "Infrared Imaging System." Hunt et al. discloses a pair of mirror systems which scan an object in two dimensions over an infrared detector.

U.S. Pat. No. 3,862,423 to Kutas et al., entitled "Scanning Thermography," proposes a scanning assembly including a scanning mirror mounted for continuous rotational scanning about one axis and oscillatory scanning about an orthogonal axis. Kutas et al. discusses the applicability of such scanning systems to medical thermography applications.

In prior art scanning thermography systems, an infrared sensor is used to convert thermal radiation into electric signals. The thermal image can be generated by means of either an optical scanning system or a pyroelectric vidicon television tube. A video monitor or the like can be used to display the image. Computer imaging technology has been deemed desirable by physicians since it is non-invasive and may require no physical contact with the body. A great deal of research has been conducted on such technology in connection with the clinical diagnosis and examination of such conditions as arthritis and phlebothrombosis, and other diseases including, notably, mastrocarcinoma (breast cancer).

The theory underlying conventional thermographic techniques as applied to cancer is that the change of the pulse distribution around a cancerous area and the rate of metabolism are greater than the general tissue, resulting in a higher temperature at the skin surface. Presently known thermography technology may have limited sensitivity and specificity, however, resulting in a high percentage of false positive and false negative assessments. The medical community's enthusiasm for thermography technology in the 1970's appeared to subside in the 1980's. In the last 10 years, it is believed that very little advancement has been made in the field of thermography.

If only the temperature of the skin surface can be measured while the relationship between the surface temperature and the emissions from the inside of the body cannot be established, then application of thermal imaging technology is limited. It is believed, therefore, that it would be desirable to provide a method and apparatus for revealing the relationship between the skin's surface radiation temperature and internal thermal radiation sources. Through image processing and measurement technology, surface or internal radiation sources can be non-invasively distinguished through extrapolation. It is believed that such technology would prove to be clinically effective in the detection and diagnosis of cancers (especially in their early stages) and other diseases.

The temperature of a live human body is between 20° C. and 40° C. at room temperature (20° C.). Differences in skin color do not significantly affect the body temperature or the emission of the thermal radiation. The wavelength of this thermal radiation is between 8 and 13 mm, which is often referred to as "infrared" region in the electromagnetic wave spectrum, the infrared region having a longer wavelength than the red or near-red spectrum. The physics of infrared radiation has been investigated extensively, and its application in thermal metabolism imaging is relatively well-known to those of ordinary skill in the art.

There are various biochemical and biophysical mechanisms that can produce heat in a live biological body. A biological body will absorb thermal energy if its temperature is below that of the environment, or will emit thermal energy if its temperature is above that of the environment. The latter condition is the preferred mode of detecting and imaging thermal metabolic activity.

Superficial (i.e., surface) thermal radiation from the skin of a biological body has previously been studied. The present invention, on the other hand, involves the thermal radiation associated with thermal conduction within the body.

There are multiple heat sources within a biological body. Although it is possible to calculate the thermal radiation from a thermal body by thermodynamics, the complexity of the boundary conditions associated with the biological body makes this approach impractical. Therefore, a practically viable method that can be used to solve the problem of imaging internal heat sources within a thermal body has not heretofore been shown. The present invention involves formulation of a new method and apparatus for analysis of a thermal system based on an analogy to electrical circuit theory; this method may be referred to herein as a "thermal-electric analogue" method.

Infrared radiation passes through a transparent medium, air, for example, at the speed of light. Thus, heat is transferred in air by thermal radiation. In a material body, on the other hand, heat transfer is based on thermal conduction resulting in establishment of thermal equilibrium. From the point of view of thermal radiation, infrared radiation deep within the body cannot be readily detected from outside. Therefore, there has not heretofore been shown a method and apparatus for resolving heat sources within the body; prior infrared imaging has been restricted to viewing objects on the surface of the body. However, in accordance with one aspect of the present invention, it is proposed that, based on the conduction of heat to establish thermal equilibrium, thermal sources lying within the body can be imaged. That is, based upon the thermal conditions at the surface of a patient's body, information about internal regions can be derived through extrapolation.

Thermal metabolism imaging systems used in clinical diagnosis are preferably not influenced by particular patient conditions or environmental conditions. Prior art thermograph machines have not been widely used because they generally do not satisfy this requirement. Accordingly, it is another aspect of the present invention that an imaging system is provided which is less sensitive disturbance from the patient and from the environment.

SUMMARY OF THE INVENTION

In accordance with one aspect of the present invention, a thermal imaging system particularly well-suited for medical diagnostic applications is provided. In one embodiment, the system includes an infrared scanning system including an infrared sensor and associated optics for scanning an anatomical area of interest, and generating electrical signals which vary in intensity according to the intensity of thermal radiation at each point in the scanned area. After digitization, the thermal energy signals are mapped to a color spectrum according to the intensity of the thermal energy at each point in the scanned image.

In accordance with another aspect of the invention, the system includes a computer for processing the thermal image data. One processing step is referred to as a thermal radiation "slice" operation, which involves gradual adjustment of the mapping of thermal intensity data to color values in a color spectrum. Displaying the thermal data during adjustment of the color mapping reveals meaningful information about internal sources of thermal energy, facilitating the detection, identification, and/or assessment of certain metabolically significant internal regions, including, for example, tumors and the like.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

The foregoing and other aspects and features of the present invention may perhaps be best appreciated with reference to a detailed description of a specific embodiment of the invention, when read in conjunction with the accompanying drawings, wherein.

DETAILED DESCRIPTION OF A SPECIFIC EMBODIMENT OF THE INVENTION

Figure 1A:
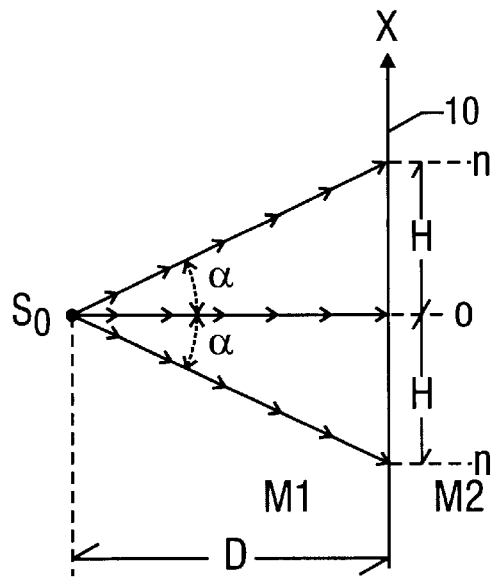
FIGS. 1a, 1b, and 1c are diagrams of a thermal system showing the distribution of thermal radiation emanating from a point heat source and impinging upon a planar surface.

As noted above, metabolic activity causes multiple heat sources to exist in a live biological body. FIG. 1a illustrates a simple case, in which a point heat source designated $S_O$ is embedded within a homogeneous medium M1, the medium M1 being further surrounded by atmosphere M2. A planar interface between medium M1 and medium M2 is identified with reference numeral 10 in FIG. 1a. Interface 10 extends along an axis designated "x" in Figure 1a.

The temperature of $S_O$, M1 and M2 are T1, T2, and T3, respectively. When T1 is greater than T2, which in turn is greater than T3, the heat transfer from $S_O$ is shown by conduction lines 12 in FIG. 1a. As shown in FIG. 1a, point heat source $S_O$ is disposed at a perpendicular distance D from interface 10. The angle of each conduction line 12 from this perpendicular is designated as α in FIG. 1a. For α not equal to zero, a conduction line intersects interface 10 at some distance x=H or x=–H from the origin (x=0), with H in the range of –n to n.

Figure 1B:
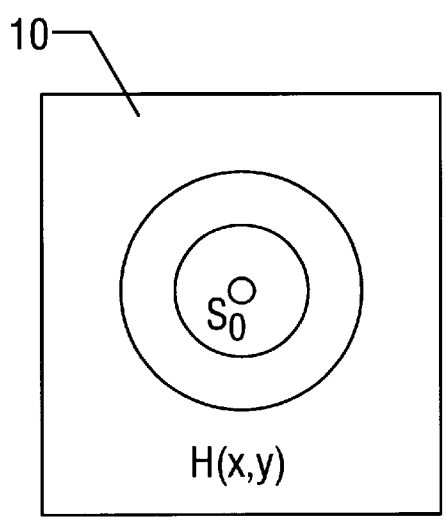
Figure 1C:
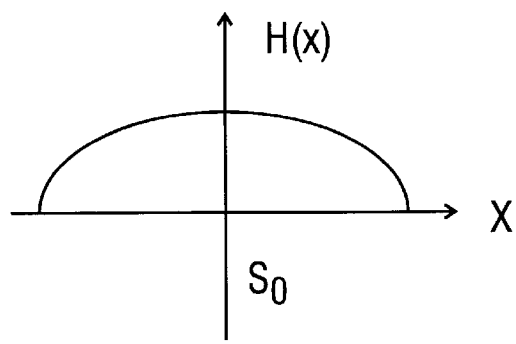

FIG. 1b shows the distribution function H(x,y) of the thermal energy radiated from point heat source $S_O$ on planar interface 10, in steady state under thermal equilibrium. H(x,y) is symmetric if the medium M1 is homogenous and the point source $S_O$ is isotropic. The pattern of H(x,y) will thus depend upon the thermal properties of medium M1 including its specific heat and heat conductivity, as well as the distance between $S_O$ and M2, i.e., the thickness of M1. FIG. 1c shows the distribution of H(x) on the x-axis.

To describe the heat conduction from the heat source $S_O$ and the thermal radiation function H(x,y), and in accordance with one aspect of the present invention, a thermal/electrical analogy can be made to relate the thermal system to its analog electric system. The correspondence between quantities in thermal and electrical systems are listed in the following Table 1:

TABLE 1

| Thermal System | Electrical System |
| --- | --- |
| Heat | Charge |
| Heat Source | Battery |
| Temperature | Voltage |
| Heat Current | Electric Current |
| Specific Heat | Electric Capacitance |
| Heat Resistance | Electric Resistance |

With reference to FIG. 1a, in medium M1 heat conduction can be thought of as many conduction lines 12 very close to each other. If it is assumed that the temperature difference and distance between $S_O$ and M2 is not large, then any given small section of conduction lines 12 itself does not represent a heat source. Under these assumptions, one of the conduction lines 12 in the thermal system in FIG. 1a can be analogized to the electrical circuit shown in FIG. 2.

Figure 2:
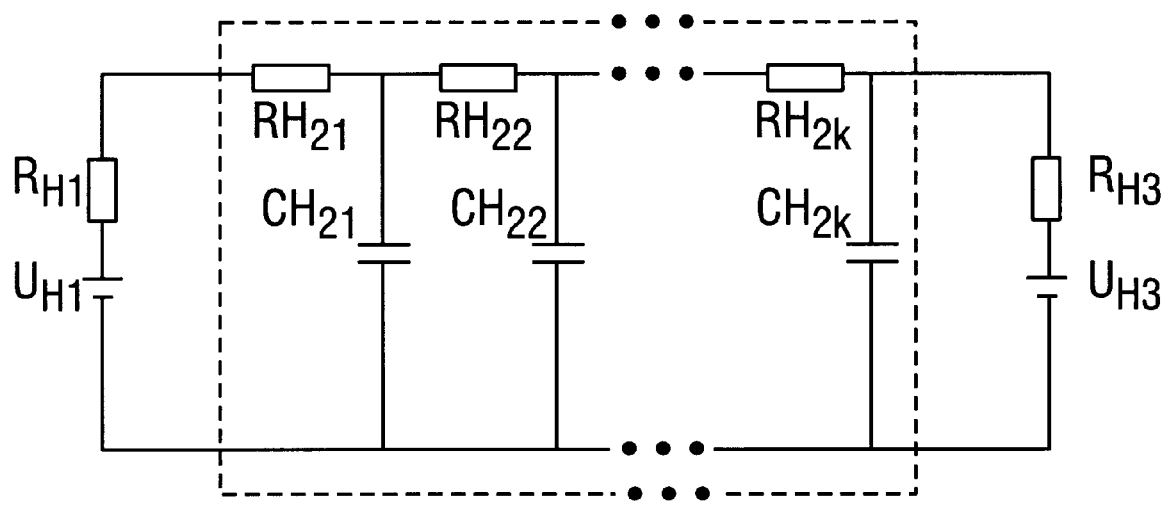
FIG. 2 is a schematic diagram of an electrical circuit analogue to the thermal system of FIG. 1.

In FIG. 2, a battery designated $U_{H1}$ is analogous to the heat source $S_O$. A battery designated UH3 represents the heat source of air (medium M2 from FIG. 1a). Resistance RH1 in FIG. 2 is the internal resistance of UH1, which accounts for the internal heat loss inside the heat source. Similarly, resistance RH3 corresponds to the heat resistance of the air. Resistances $RH_{21}$ through $RH_{2K}$ correspond to the heat resistance of the medium M1, specifying the heat loss per unit length of a conduction line 12 within M1. $CH_{21}$ through to $CH_{2K}$ represent the heat capacity of the medium M1, specifying the heat reserve per unit length of a conduction line within M1. Using the circuit of FIG. 2, conventional circuit analysis can be applied, assuming the circuit is under steady state, to obtain an expression for the transfer function H(x) as follows:

$$H(x) = \sum_{x=-n}^{n} \left[ U_{H1} - \frac{\sum_{i=1}^{x} R_{H2i}}{R_{H1} + R_{H3} + \sum_{i=1}^{x} R_{H2i}} \times (U_{H1} - U_{H3}) \right]$$

where $$n = int\left(\frac{d}{\cos\alpha}\right)$$

α being the angle of incidence of a given conduction line 12 with plane 10, as noted above with reference to FIG. 1a, and d being given by the equation $$d = int\left(\frac{D}{R_0}\right)$$

where D is the distance along the x axis between point heat source $S_O$ to interface 10 and $R_O$ is the heat resistance rate of homogenous medium M1.

Thus, along the x axis, the relative radiation distribution is as shown in FIG. 1c, and on the plane A we get a circular radiation distribution with diameter 2H, as shown in FIG. 1b, which is highest in the center and gradually decreases as |x| increases.

For an interface 10 having transverse thermal conduction is 3 to 5 times lower than internal conduction within medium M1, when α=45° then H=D and hence D/r=0.707. This is referred to as the "half power point."

In an unsteady state, the thermal radiation as a function of time can be used to study the heat transfer and equilibrium establishment in the medium, such as when additional cold or heat sources are introduced near the medium, or when the metabolism is changing, for example, during exercise.

When multiple heat sources exist within a medium, the distribution of H(x,y) can be calculated as the superposition of the H(x,y) from multiple single point sources. If the medium M1 is not homogeneous, the inhomogeneity can be simplified to calculate H(x,y) on the plane A. The following examples show a few typical cases of thermal distributions H(x,y). In each of these examples, the designation conventions adopted in FIGS. 1a–1c are used; that is, conduction lines are designated with reference numeral 12, the angles of conduction lines 12 with respect to the perpendicular distance between point heat source $S_O$ and plane 10 are designated as α, and so on.

Figure 3A:
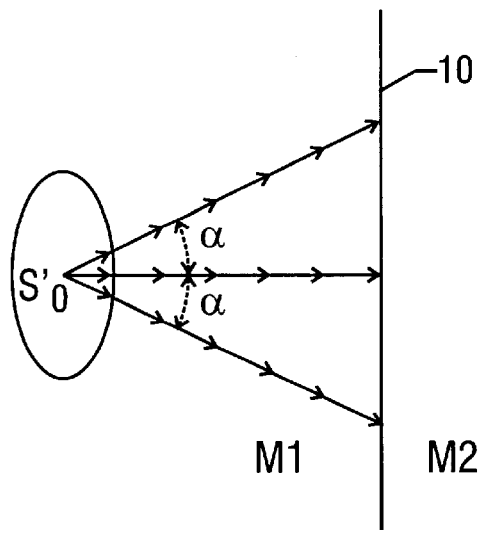
FIGS. 3a, 3b, and 3c are diagrams of a thermal system showing the distribution of thermal radiation emanating from a uniform circular heat source and impinging upon a planar surface.
Figure 3B:
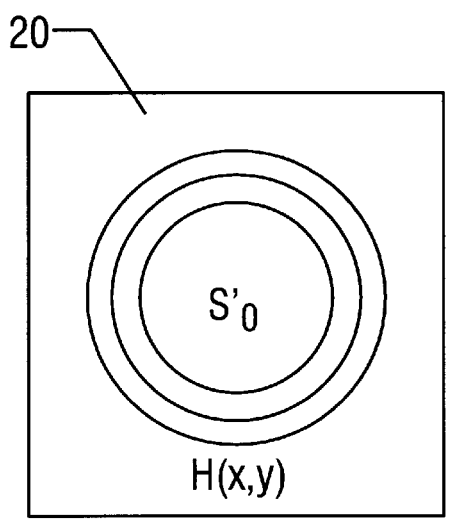
Figure 3C:
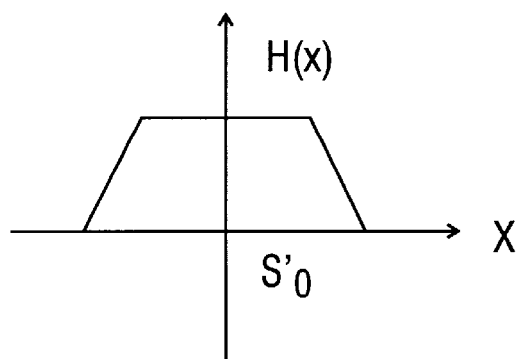

FIG. 3a shows a heat source $S_O'$ having a circular, planar configuration. The thermal energy distribution H(x,y) on plane 10 is again symmetric and circular, as shown in FIG. 3b. As shown in FIG. 3c, H(x) along the x axis on plane 10 has a trapezoidal distribution. The relative width of the sides of the trapezoid decreases when source $S_O'$ is farther away from plane 10. As the distance between the source $S_O'$ and plane A increases, the source distribution approaches that of a point source, as previously discussed with reference to FIGS. 1a–1c.

Figure 4A:
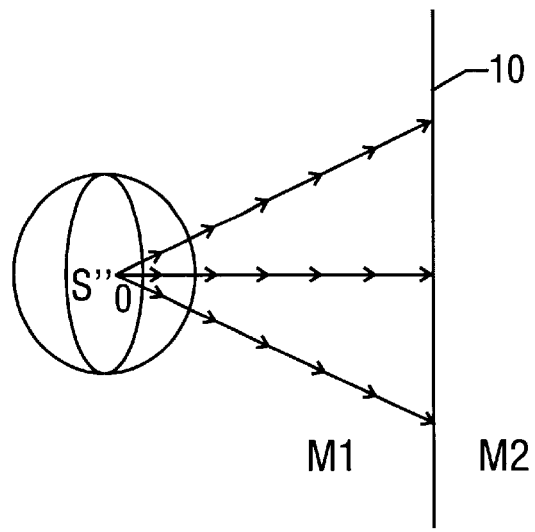
FIGS. 4a, 4b, and 4c are diagrams of a thermal system showing the distribution of thermal radiation emanating from a three-dimensional Gaussian distributed spherical heat source and impinging upon a planar surface.
Figure 4B:
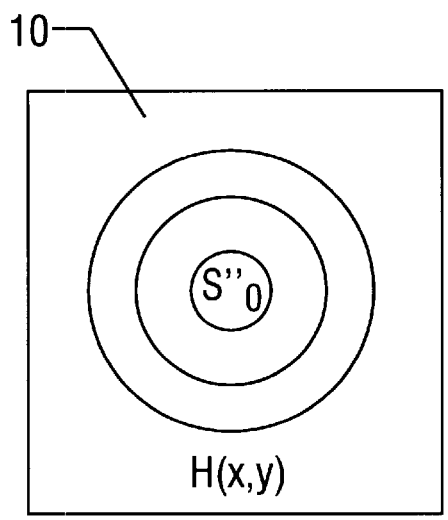
Figure 4C:
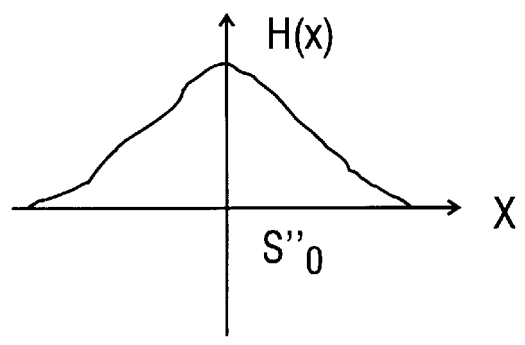

FIG. 4a shows a non-uniform, three-dimensional Gaussian distributed spherical heat source $S_O''$. Again, the thermal distribution function H(x,y) shown in FIG. 4b is substantially circular. However, as shown in FIG. 4c, the energy on the x-axis is has a Gaussian distribution. Again, the distribution approaches that of a point source (FIGS. 1a–1c) as the distance D between the source and plane 10 increases.

Figure 5A:
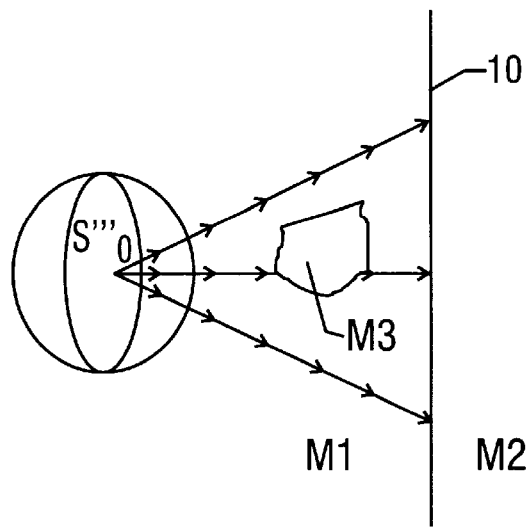
FIGS. 5a, 5b, and 5c are diagrams of a thermal system showing the distribution of thermal radiation emanating from a three-dimensional Gaussian distributed spherical heat source, radiating through an inhomogenious medium and impinging upon a planar surface.
Figure 5B:
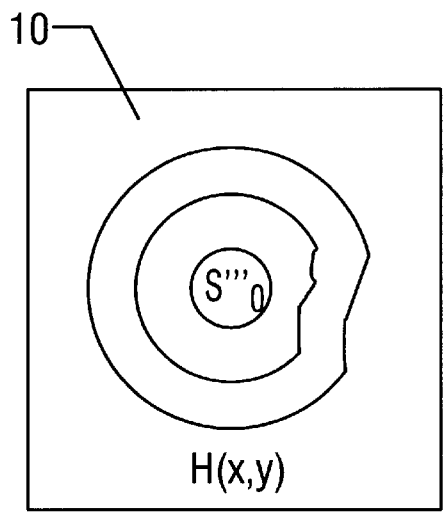
Figure 5C:
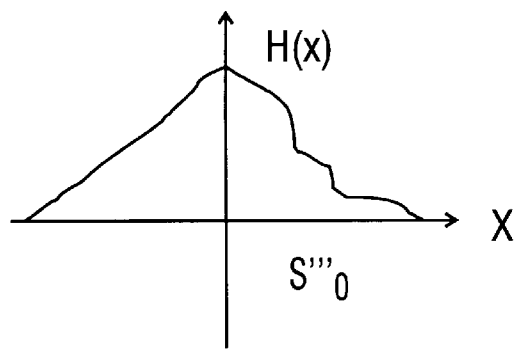

In the foregoing examples, it has been assumed that M1 was a homogenous medium. FIGS. 5a–5c illustrate an example of a non-uniform, three-dimensional Gaussian distributed spherical heat source $S_O'''$ within an inhomogeneous medium. The inhomogeneity is represented by a inhomogenous region designated M3 in FIG. 5a. As shown in FIGS. 5b and 5c, the inhomogeneity of the medium introduces perterbations in the thermal transfer distribution functions H(x,y) and H(x) as compared with those functions corresponding to the same spherical heat source in a homogenous medium, previously discussed with reference to FIGS. 4b and 4c.

The examples of FIGS. 1a–1c, 3a–3c, 4a–4c and 5a–5c serve to illustrate the theory underlying the present invention. In accordance with one aspect of the present invention, a thermal radiation image of one part of human body is obtained, and information about internal metabolic activity is detected, derived and/or extrapolated based upon the fundamental principles of thermal conduction illustrated in the foregoing examples. That is, the skin surface plays the role of planar interface 10 in the foregoing examples, such that thermal radiation patterns at the skin surface can be used to extrapolate information about underlying internal metabolic activity, which constitutes the heat source $S_O$ in the examples.

Internal heat sources at different depths and having different shapes are reflected in different surface patterns in the image. From the above analyses, it is believed that the thermal radiation pattern at the skin surface can be detected, observed and measured, and used to calculate the center point temperature $U_O$. Image processing technology can then be applied to determine the half power point (i.e., 0.707$U_O$), the distance between the half power point and the skin surface being the depth D of the source.

For different parts of a human body, the heat resistance rate (thermal conductivity) is different. For example, for fatty tissue (adipose), the heat resistance rate R is on the order of 0.1 to 0.15° C./cm. For muscle R is on the order of 0.2° C./cm, and for bone, R is generally in the range 0.3 to 0.6° C./cm.

Thus, in accordance with one aspect of the present invention, the temperature of intra-body (i.e., internal) heat sources can be non-invasively ascertained. The difference between this temperature and normal metabolic thermal radiation temperature is the very useful data, and it can be used to detect and/or diagnose the nature and characteristics of lesions or pathology within the body.

The following Table 2 lists the heat production of various cells relative to normal cells. From the heat generated from a group of cells, the physiological properties of the cells can be analyzed and the pathological features of the tissues can be diagnosed.

TABLE 2

| | Normal Cells | Bone | Lifeless Cells | Benign Mass | Chronic Infection | Acute Infection | Malignant Mass |
|---|---|---|---|---|---|---|---|
| Relative Heat | 0 ~ 0.5 | −0.5 ~ −1.0 | −1.5 ~ −4.0 | −0.2 ~ −1.0 | −0.5 ~ 1.0 | 1.0 ~ 2.0 | >2.8 |

To reduce the influence of the measurement distance from the patient to the scanner, in addition to multiple levels of filtering, a detector sensitive only to radiation wave length rather than to radiation intensity is preferable.

Among all the factors affecting the thermal radiation from the patient, the most important factor is the patient. The thermal radiation could be affected by the patient's mental status, psychological or physiological conditions, or other environmental disturbance. The normal basal body temperature among different patients can also differ significantly, i.e., by more than 6 degrees or so. In the prior art, the normal basal temperature of the human body or a particular anatomic region was averaged from the human population to be used as a diagnostic standard. This can result in large errors in diagnostic specificity because of the thermal differences existing among different people.

It has been proposed to use the temperature differences of the corresponding anatomic regions as a diagnostic standard. This can lead to somewhat improved diagnostic specificity, but it still may not satisfy the clinical requirement. In accordance with one aspect of the present invention, therefore, it is proposed to use the normal metabolic thermal radiation temperature of the a patient himself/herself within the same body region as the reference temperature value. Clinical trials have shown great improvement of the diagnostic specificity. The method and apparatus of the present invention avoids the errors due to: (1) the difference in basal normal temperature among the population; (2) the disturbance from the patient himself/herself; and (3) disturbances from the environment.

In principle, the metabolic regions from which the normal basal temperature of the patient is obtained include head, extremity, chest, abdominal, dorsal regions, and other large and uniform areas on the body. The selection of the normal regions should avoid inclusion of the diseased, adipose, or bony areas.

Figure 6:
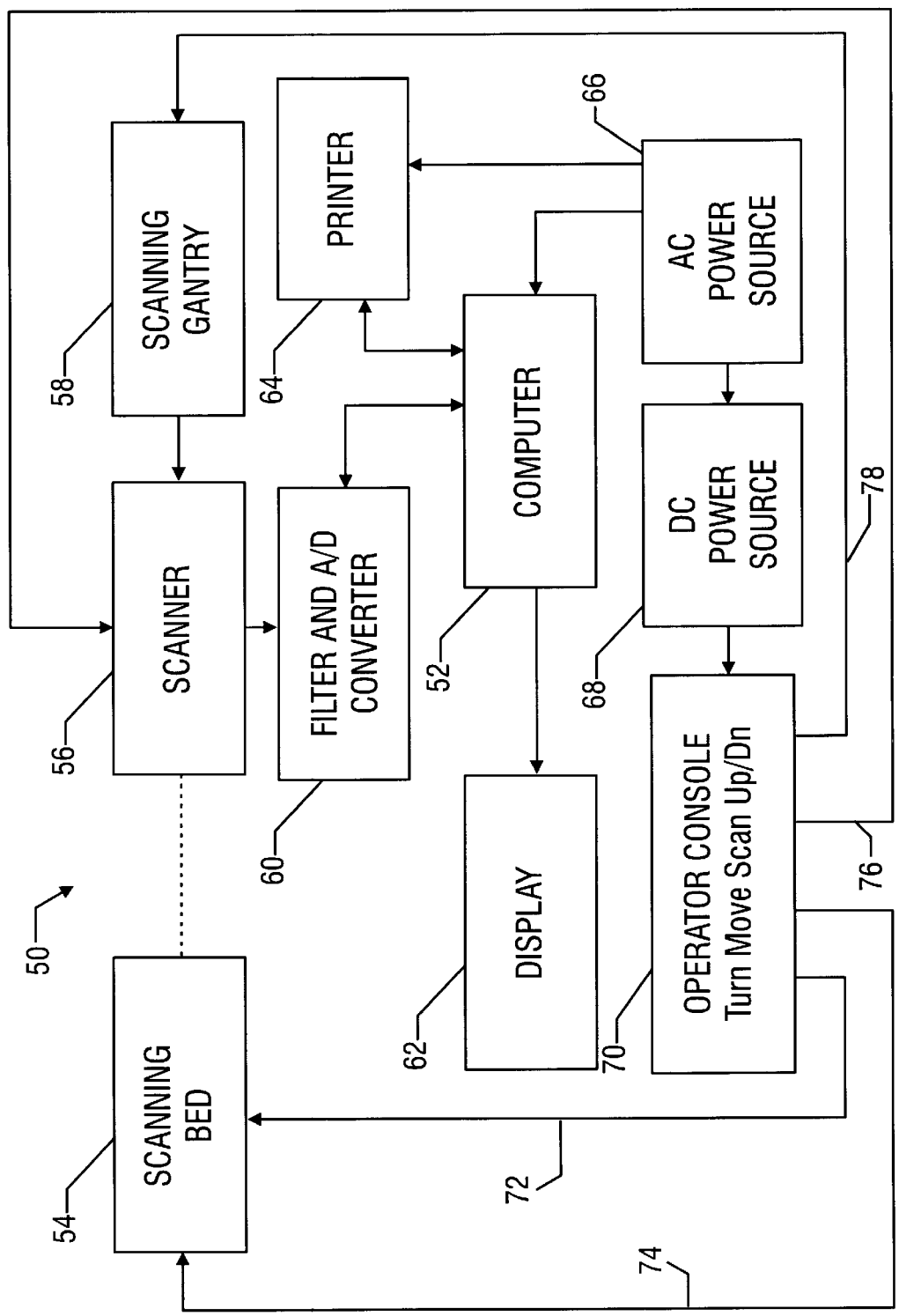
FIG. 6 is a block diagram illustrating a thermal imaging system in accordance with a specific embodiment of the present invention.

FIG. 6 is a block diagram of a thermal imaging system 50 in accordance with one embodiment of the present invention. Central to the system 50 is a computer 52, which in the presently preferred embodiment of the invention is an industry-standard personal computer system including a microprocessor, such as the commercially-available Intel Pentium™ processor or the like, operating under control of, for example, the Windows 95™ operating system. Those of ordinary skill in the art, however, will appreciate that various other types of computers now available or to become available may be equally or even more suitable for the purposes of practicing the present invention. For the purposes of the present disclosure, it will be assumed that computer 52 is a system which includes such conventional and well-known components as a hard disk drive, keyboard, mouse or other cursor control device, and so on.

In use, a patient upon whom thermographic imaging in accordance with the method and apparatus of the present invention is to be performed is positioned on a scanning bed 54, within the scanning field of a scanner 56 carried by a scanning gantry 58. The scanner 56 of the presently disclosed embodiment will be hereinafter described in further detail. As would be appreciated by those of ordinary skill in the art, scanner 56 functions in a conventional manner to generate electrical signals corresponding to the intensity and wavelengths of electromagnetic radiation present in its scanning field. Various scanning systems have been shown in the art, and although the present disclosure will describe one or more scanners in detail, it is believed that the particular details of the implementation of the scanning system employed to obtain infrared data is not critical to an understanding of the principles underlying the present invention, and it is further believed that those of ordinary skill in the art having the benefit of the present disclosure would be readily able to adapt the teachings of the present disclosure to the purposes of practicing the present invention.

The electrical signals from scanner 56 are provided as input to an analog-to-digital (A/D) converter and filtering circuit 60, which performs a filtering and digitization function on the scanner's output. The digitized scanning signals are then available for processing by computer system 52. The resulting processed images may then be displayed on display 62, which may be a high-resolution video monitor or the like. The processed images may also be output to a printer 64.

The remaining components of thermographic imaging system 50 are more or less conventional in design and operation. For example, an AC power supply 66 is used to provide power to various components of system 50. A DC power supply 68 converts AC power from AC power supply 66 to DC, providing the necessary operational power for an operator console 70. Console 70 is the means by which an operator of system 50 controls the activation, movement and positioning of scanning bed 54, scanning gantry 58 and scanner 56. For example, a "Turn" signal from operator console 70 is provided on line 72 to cause scanning bed 54 to turn. Similarly a "Move" signal on line 74 controls lateral movement of scanning bed 54. A "Scan" signal on line 76 is provided to scanner 56 for controlling activation and deactivation of scanner 56. An "Up/Down" signal provided to scanning gantry 58 controls up and down positioning of gantry 58 and scanner 56.

Figure 7:
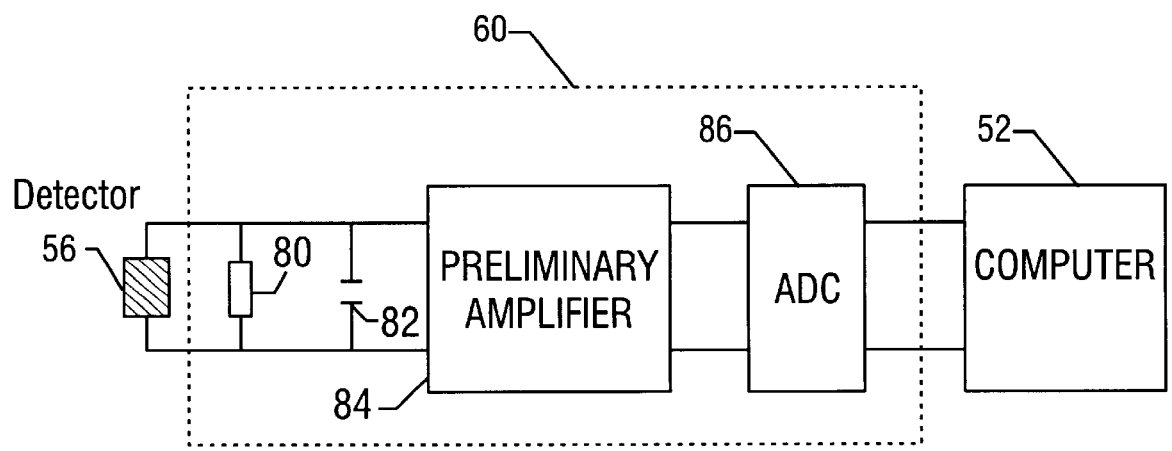
FIG. 7 is a schematic/block diagram of a portion of the system from FIG. 6 including scanner, filter, and analog-to-digital converter subsystems.

FIG. 7 is a slightly more detailed block diagram of a portion of infrared scanning/imaging system 50 in accordance with the presently disclosed embodiment of the invention, including filter and A/D converter circuit 60, computer system 52, and scanner 56. As will be hereinafter described in further detail (in particular, with reference to FIGS. 11 and 12), scanner 56 includes an infrared detector 98 and various optics and focusing systems to scan an image field and generate electrical signals representing a matrix of thermal energy intensity values (256×256 values, in the presently disclosed embodiment, although those of ordinary skill in the art will appreciate that greater or lesser resolution may be implemented).

The output from scanner 56 is first applied to a low-pass filter circuit comprising a resistor 80 (a 100Ω resistor in the presently preferred embodiment) and a capacitor 82 (a 0.01 μF capacitor in the presently preferred embodiment). This low-pass filtering reduces the electronic disturbance or noise from other equipment which might be present in the clinical environment in which system 50 is used. In the presently disclosed embodiment, the filter comprising resistor 80 and capacitor 82 attenuates signals over 100 kHz by 40 dB or so.

With continued reference to FIG. 7, the filtered output from infrared detector 98 is applied to a preamplifier, as would be familiar to those of ordinary skill in the art, and then applied to the input of A/D converter 86. In the presently disclosed embodiment, A/D converter 86 operates at 100 kHZ with 12-bit resolution. The digitized sensor signal is then provided as input to computer 52 for digital processing in accordance with one aspect of the present invention.

Figure 8:
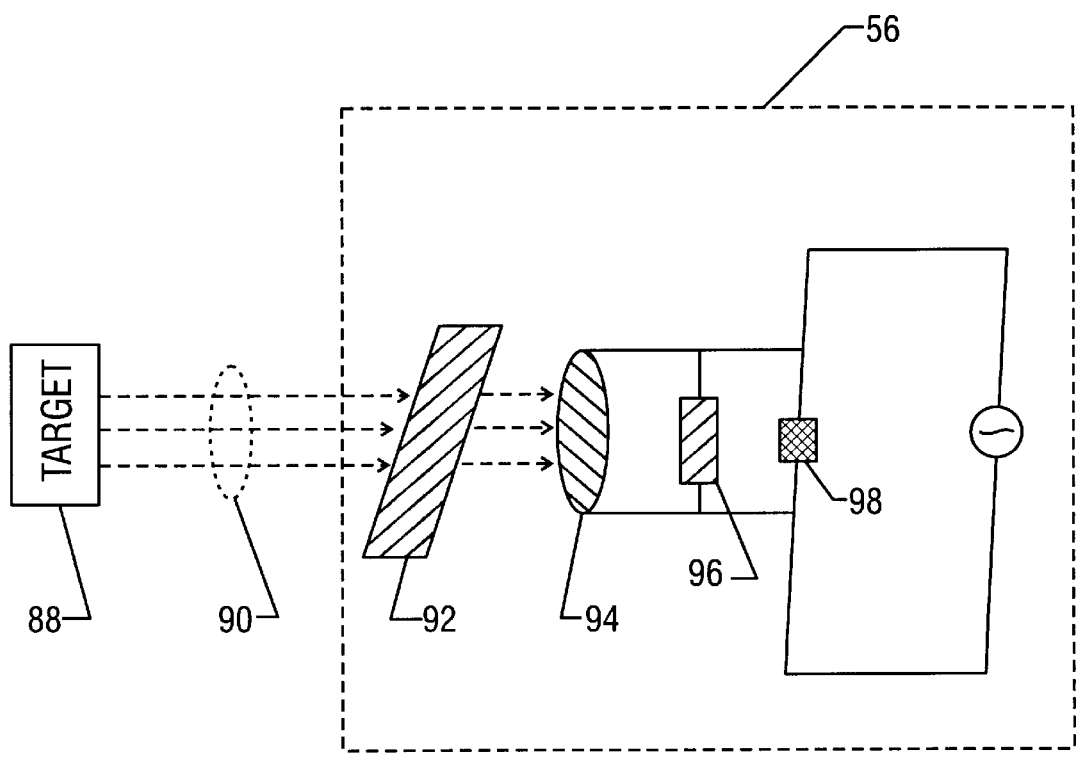
FIG. 8 is a schematic/block diagram of the scanner subsystem from the system of FIG. 6.

Turning now to FIG. 8, there is shown a schematic/block diagram of a portion of the thermal imaging system 50 in accordance with the presently disclosed embodiment of the invention, illustrating, in particular, certain details of scanner 56. In FIG. 8, the target being thermally scanned and imaged, i.e., an area of the patient's anatomy, is represented with reference numeral 88. Thermal (i.e., infrared) radiation from target 88 is represented with dashed lines 90 in FIG. 8. In accordance with one aspect of the present invention, in order to reduce the influence of the measurement distance between target 88 and scanner 56, multiple levels of radiation filtering are employed. Additionally, scanner 56 is preferably sensitive only to radiation wavelength, and not to radiation intensity.

As shown in FIG. 8, the thermal radiation 90 first passes through a Germanium monocrystal filter, designated with reference numeral 92. Germanium monocrystal filter 92, as will be appreciated by those of ordinary skill in the art, has a transmission fraction of approximately 90% to radiation having a wavelength of between 8 and 13 μm (typically referred to as "infrared" radiation), and a transmission fraction of less than 0.1% to visible light.

Scanner 56 further includes a Germanium coated lens 94 having transmission characteristics substantially the same as discussed above with reference to Germanium monocrystal as well as a further Germanium monocrystal filter 96.

The three levels of Germanium filtration just described preferably result in a transmission fraction of less than 0.1% for radiation beyond 8 to 13 μm, and less than 0.001% to visible light for the radiation actually impinging upon the wavelength sensitive detector designated with reference numeral 98 in FIG. 8. This reduces the system's overall sensitivity to environmental light.

Figure 9A:
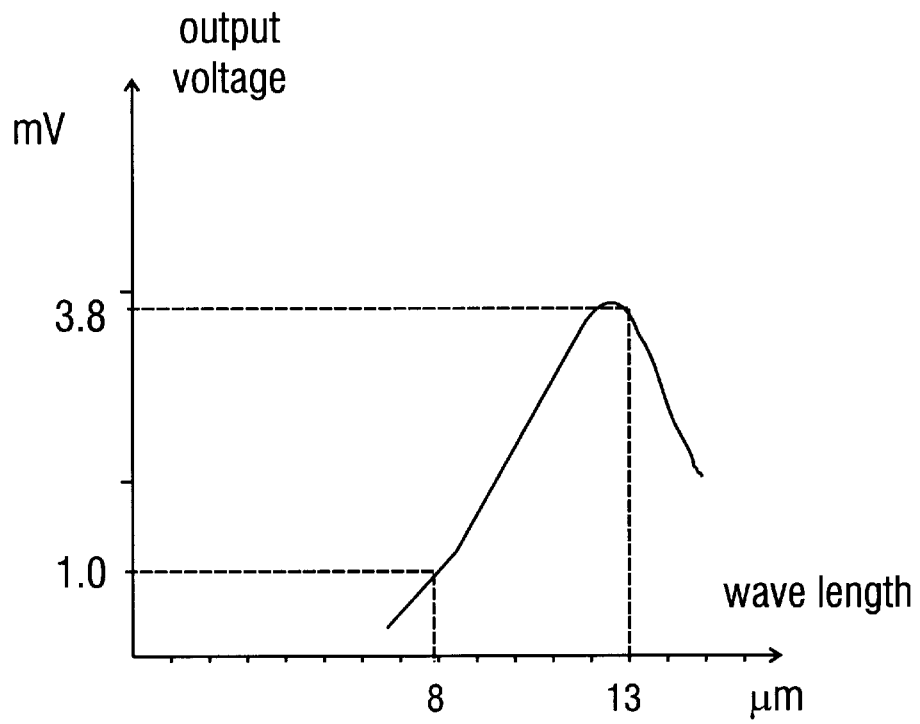
FIGS. 9a and 9b are graphs of the output response of the scanner subsystem from FIG. 8.
Figure 9B:
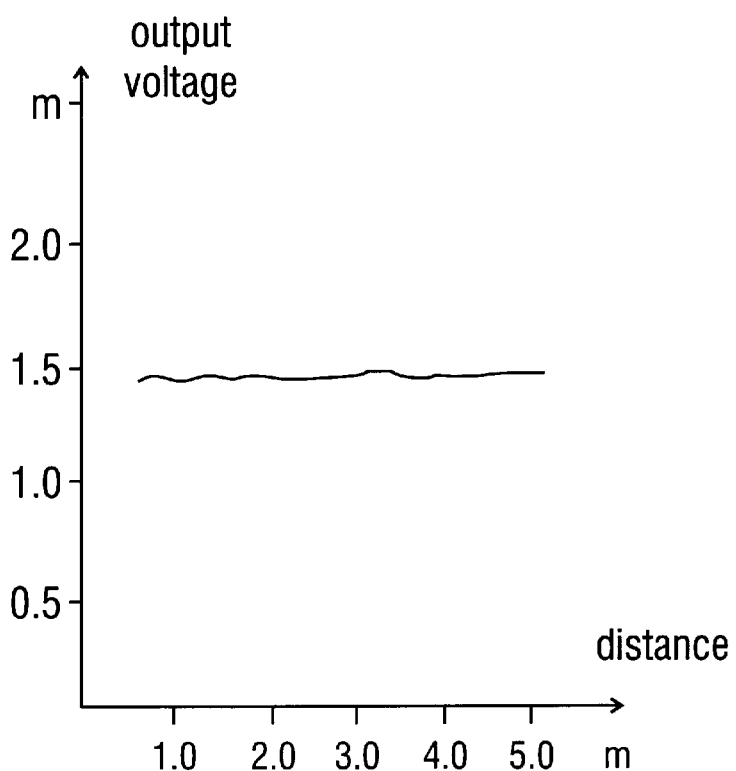

Wavelength sensitive detector 98 in the presently disclosed embodiment of the invention is made of Cd-Hg-Te material. Various infrared detectors suitable for the purposes of practicing the present invention are known in the art and are commercially available. U.S. Pat. No. 5,034,794 to Murotani, entitled "Infrared Imaging Device" is but one example. FIGS. 9a and 9b illustrate the output response for sensor 98 in accordance with the presently disclosed embodiment of the invention. In particular, FIG. 9a shows the output voltage of sensor 98 as a function of wavelength, and it can be seen from FIG. 9a that the output response is greatest in the wavelength range of 8 to 13 μm. FIG. 9b shows the output voltage of sensor 98 as a function of the distance between sensor 98 and target 88. It is apparent from FIG. 9b that the output response as a function of distance is relatively flat, rendering system 50 relatively insensitive to variations in distance between scanner 56 and target 88.

In the presently disclosed embodiment of the invention, wavelength sensitive detector 98 preferably enables the scanner to detect temperatures in the range from 0 to 50° C., with an accuracy of 0.05° C. In the presently implemented embodiment, a scan takes approximately five seconds, resulting in a 256×256×8 bit (64 kByte) image.

Although the present invention is described herein as incorporating a "single-point" infrared sensor, i.e., a sensor which is capable of detecting infrared radiation at a single point within the overall scanning area, it is contemplated that other infrared scanning devices, currently known or to be developed, may be advantageously employed in the practice of the present invention. For example, linear or two dimensional (e.g., grid) arrays of multiple individual sensors are known, and it is believed that those of ordinary skill in the art having the benefit of the present disclosure would be able to readily adapt the presently disclosed embodiment of the invention to incorporate such different types of sensors for the purposes of practicing the present invention. A potential advantage of using a linear or two-dimensional arrays of sensors would be a reduction in the time necessary to scan a given image area. It is to be understood, therefore, that the present invention is in no way limited to systems incorporating a single-point sensor.

Figure 10:
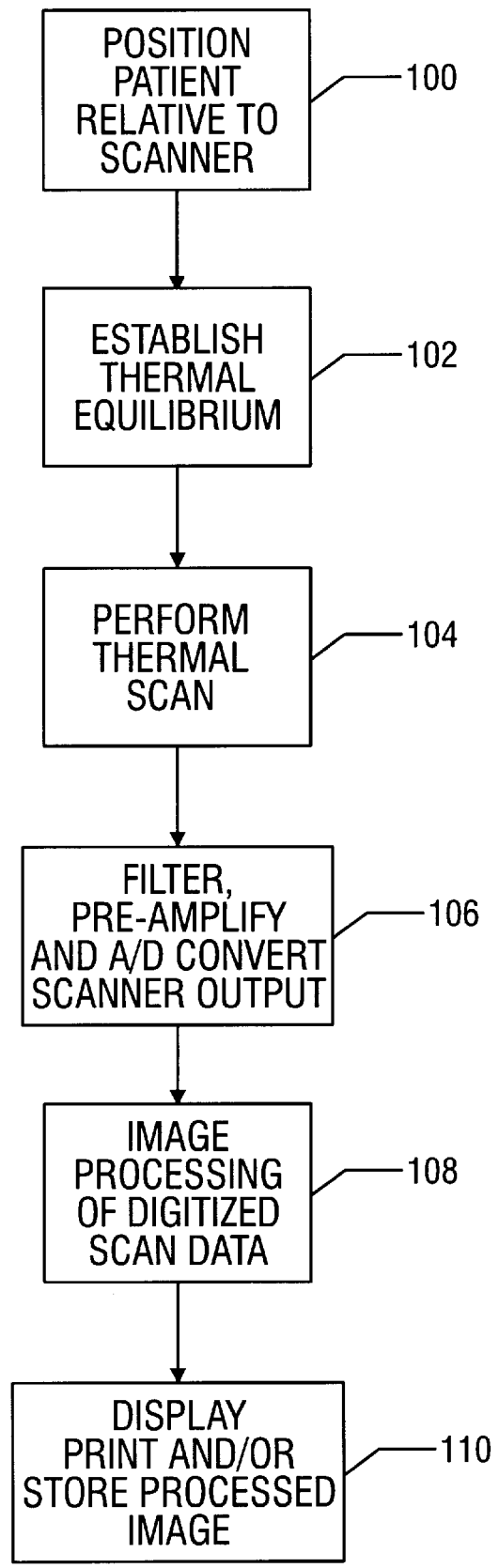
FIG. 10 is a flow diagram illustrating operation of the thermal imaging system of FIG. 6.

FIG. 10 is a flow chart illustrating operation of system 50 in accordance with the presently disclosed embodiment of the invention. The first step of system operation, positioning the patient with respect to the scanner, is represented by block 100 in FIG. 10. To facilitate this, system 50 provides for movement of both scanning bed 54 and scanning gantry 58 carrying scanner 56, as previously described. In the presently disclosed embodiment of the invention, scanning gantry 58 is preferably capable of moving from between 0.4 to 1.6 meters from scanning bed 54. Moreover, gantry 58 is preferably capable of rotating ±45° left and right, and ±30° up and down. All such positioning of gantry 58 is faciliated by the operator console 70, previously discussed reference to FIG. 6.

Similarly, scanning bed 54 is preferably capable of positional adjustment with respect to gantry 58. In the presently disclosed embodiment, scanning bed 54 is preferably capable of from between 0.3 and 5.0 meters from scanning gantry 58, and of turning 360° with respect to gantry 58.

With continued reference to FIG. 10, the next step in the operation of system 50 is to ensure that thermal equilibrium has been established; this is represented by block 102 in FIG. 10. Because of the specific heat of the human body, thermal conduction and establishment of thermal equilibrium in the human body can be a slow process. Thus, it may require up to 10 to 15 minutes prior to an examination to achieve a thermal equilibrium condition. On the other hand, the dynamic thermal process can be used to study and measure the specific heat of the human bodies, as well as to assess pathological or other body reactions.

The next step in the operation of system 50 is to initiate the scanning operation, as represented by block 104 in FIG. 10. During this operation, thermal radiation from the scanned area of the patient is received by scanner 56 and transformed into analog electrical signals, as previously discussed.

These analog signals are filtered, preamplified, and applied to the input of A/D converter 86, as also previously discussed, and as represented by block 106 in FIG. 10. The digitized signals are then provided to computer 52 for processing, as represented by block 108 in FIG. 10. The digitized signals received by computer 52 represent a two-dimensional color image reflecting skin surface temperature of the scanned area. Processing by computer 52, applying the concepts of extrapolation discussed with reference to the examples of FIGS. 1a, 1b, 1c, 3a, 3b, 3c, 4a, 4b, 4c, 5a, 5b, and 5c is necessary to derive a two-dimensional image representing the metabolic activity within the patient's body at the scanned area.

Finally, as represented by block 110 in FIG. 10, the resulting processed image, representing an extrapolation of the surface thermal image to represent internal metabolic activity, can be displayed, printed, and/or stored by thermal imaging system 50.

It is contemplated that system 50 may be capable of various image processing and diagnostic functions, as would be appreciated by those of ordinary skill in the art, including, but not limited to: providing a heat source enhance function, whereby 256 colors can be used to represent temperature differentials of anywhere from 0.01 to 0.1° C.; measurement of heat radiation at multiple points on the patient; computing the maximum, minimum, and/or mean temperature within a scanning area; displaying distribution curves of heat radiation in any horizontal or vertical direction; multiple image comparison; and generation of three-dimensional images.

Figure 11:
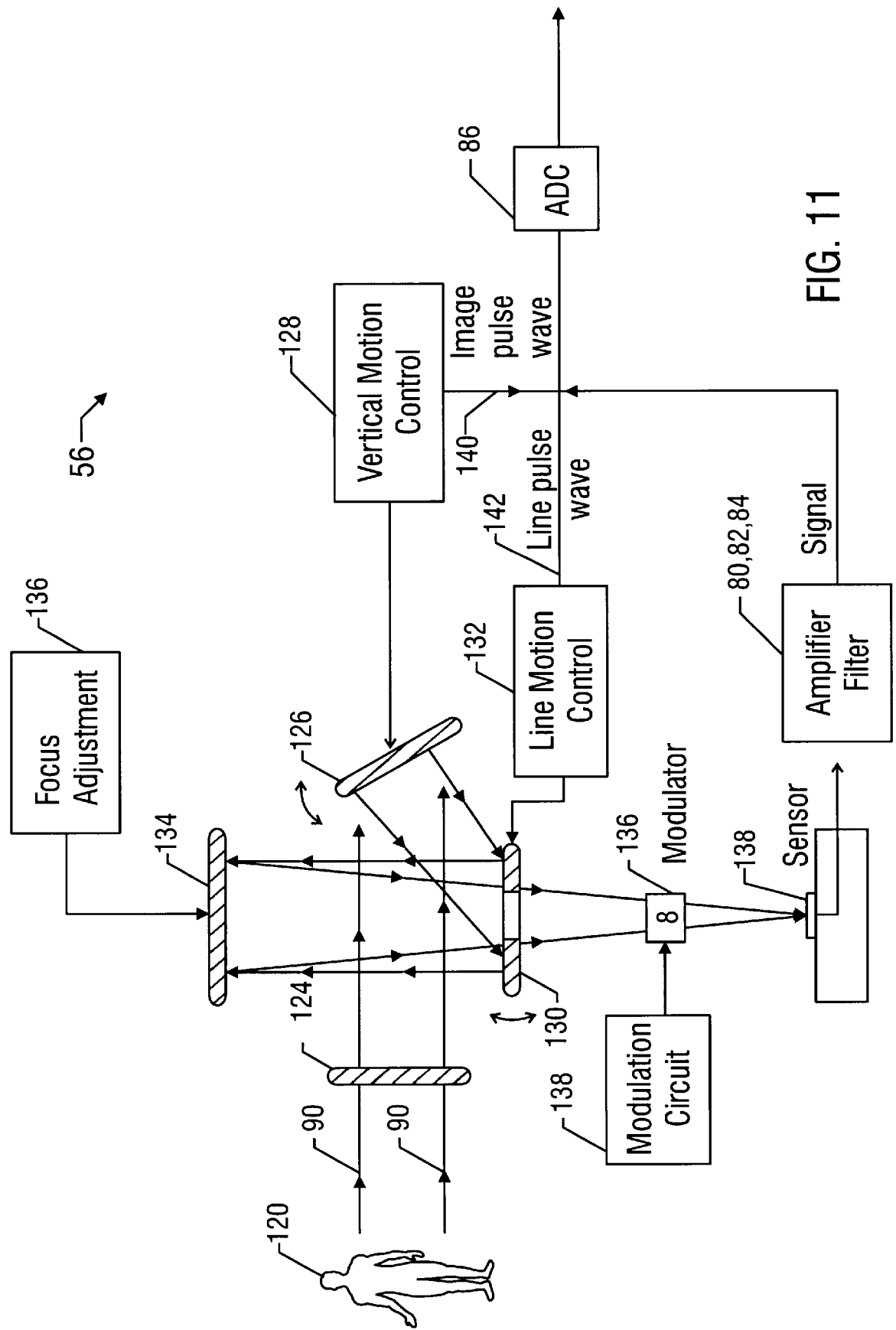
FIG. 11 is a schematic/block diagram of the scanner subsystem in the imaging system of FIG. 6.
Figure 12:
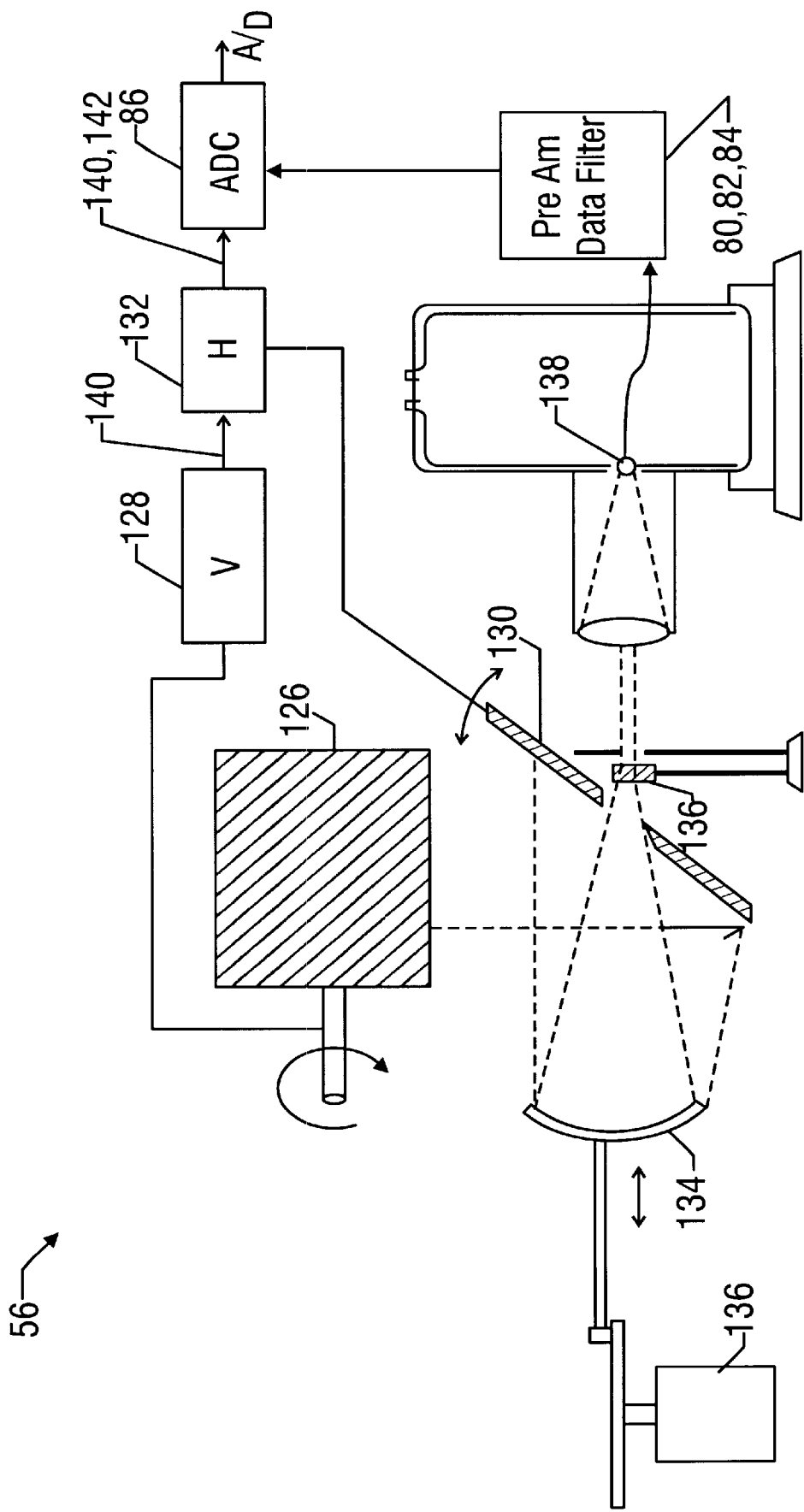
FIG. 12 is an alternative schematic/block diagram of the scanner subsystem in the imaging system of FIG. 6.

Turning now to FIGS. 11 and 12, there are provided alternative schematic/block representations of the scanning system 56 in accordance with the presently disclosed embodiment of invention. It is to be understood that FIGS. 11 and 12 are intended to represent the same scanning system 56; system 56 is merely represented in FIGS. 11 and 12 from different perspectives and with different levels and styles of schematic detail. Accordingly, identical reference numerals are used in FIGS. 11 and 12 to represent the same components.

Scanning system 56 as represented in FIGS. 11 and 12 operates as follows: Thermal radiation from patient 120, represented by ray traces 90 in FIGS. 11 and 12 (as it was in FIG. 8), passes through front optics 124, which includes germanium monocrystal 92, germanium filter 94 and germanium lens 96, previously described with reference to FIG. 8.

Next, thermal radiation 90 impinges upon a vertical optics system 126, an oscillating reflective system responsible for effectuating scanning in the vertical direction. Vertical optics system 126 is controlled by a vertical motion control circuit 128.

Thermal radiation 90 is then reflected to impinge upon a horizontal or line optics system 130, also an oscillating reflective system responsible for effectuating scanning in the horizontal direction. Line optics system 130 is controlled by a line motion control circuit 132.

From line optics system 130, the thermal radiation is reflected to a focusing optics system 134 which is controlled by a focus adjustment circuit 136. Focusing optics system 134 operates to focus the thermal radiation 90 upon a modulator 136. Under control of a modulation circuit 138, the vibrations of modulator 136 are used to control the optimal linear sampling of scanner mirror 130 during the scanning to ensure that the distortion of images are minimized. Moreover, the thermal radiation will be shielded during the back scanning period of the scanner mirror 130.

The output of modulator 136 is applied to a sensitive infrared sensor 138, which in the presently disclosed embodiment of the invention is a point type sensor although it is to be understood that other commercially-available infrared sensors may be suitable for the purposes of practicing the present invention. In particular, as noted above, it is contemplated that linear or two-dimensional arrays of multiple sensors can be employed.

As previously noted with reference to FIGS. 6 and 7, the output of sensor 138 is fed to an amplifier and analog-to-digital converter (ADC) circuit 60, which as shown in FIG. 7 comprises resistor 80, capacitor 82, amplifier 84 and ADC 86.

Referring to FIG. 11, vertical motion control circuit 128 and line (horizontal) motion control circuit 132 generate signals for synchronizing the horizontal and vertical scanning of scanner 56, in a conventional way. Vertical motion control circuit 128 generates a signal "frame synch pulse wave" on a line designated with reference numeral 140 and line motion control circuit 132 generates a signal "line synch pulse wave" on a line designated with reference numeral 142 in FIG. 11.

Figure 13:
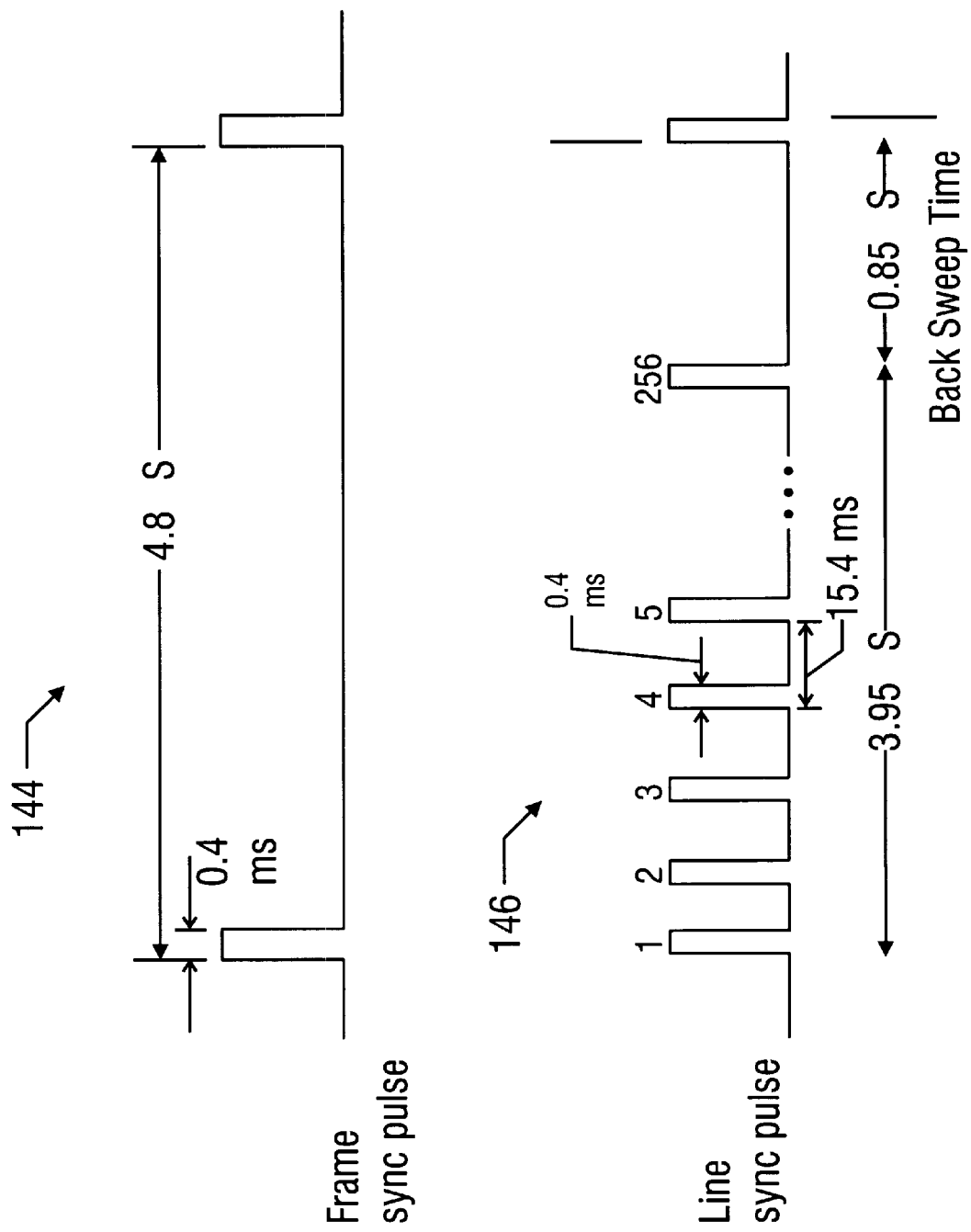
FIG. 13 is a plot of an image pulse wave and a line pulse signal present in the scanning subsystem of FIGS. 11 and 12.

The frame synch pulse wave and line synch pulse wave signals are depicted in FIG. 13. In the presently disclosed embodiment of the invention, the image synch pulse wave signal, designated generally with reference numeral 144 in FIG. 13, is a periodic wave of pulses of 0.4 mSec duration occurring every 4.8 sec, while the line synch pulse wave signal is a series of 256 pulses of 0.4 mSec duration pulses occurring every 15.4 mSec, followed by a 0.85 sec "back-sweep" interval prior to a subsequent series of 256 pulses.

Image scanning occurs as follows: when a scan is initiated, a frame synch pulse and the first of 256 line synch pulses is generated. One frame consists of 256 horizontal scan lines. One line is scanned for every line synch pulse in line synch pulse wave 146. After 256 lines have been scanned, the 0.85 sec back sweep time occurs, enabling the vertical motion control circuit to redirect the scanner to the top of the image, whereupon another frame synch pulse occurs signalling the start of another image scan.

It is to be understood that the particulars of the scanning arrangement described above, and of the nature of the frame synch pulse wave 144 and line synch pulse wave 146 may be varied from implementation to implementation. For example, if a different type of sensor (e.g., a linear or two-dimensional array) were used in a given implementation, the timing of horizontal and/or vertical scanning may be correspondingly different. It is believed that those of ordinary skill in the art having the benefit of the present disclosure would be readily able to adapt the present disclosure in accordance with such design and implementation variations.

The image pulse wave and line pulse waves signals are also provided to ADC 86 in order to enable ADC 86 to synchronously convert the analog output from scanner 56 to digital values.

Figure 14:
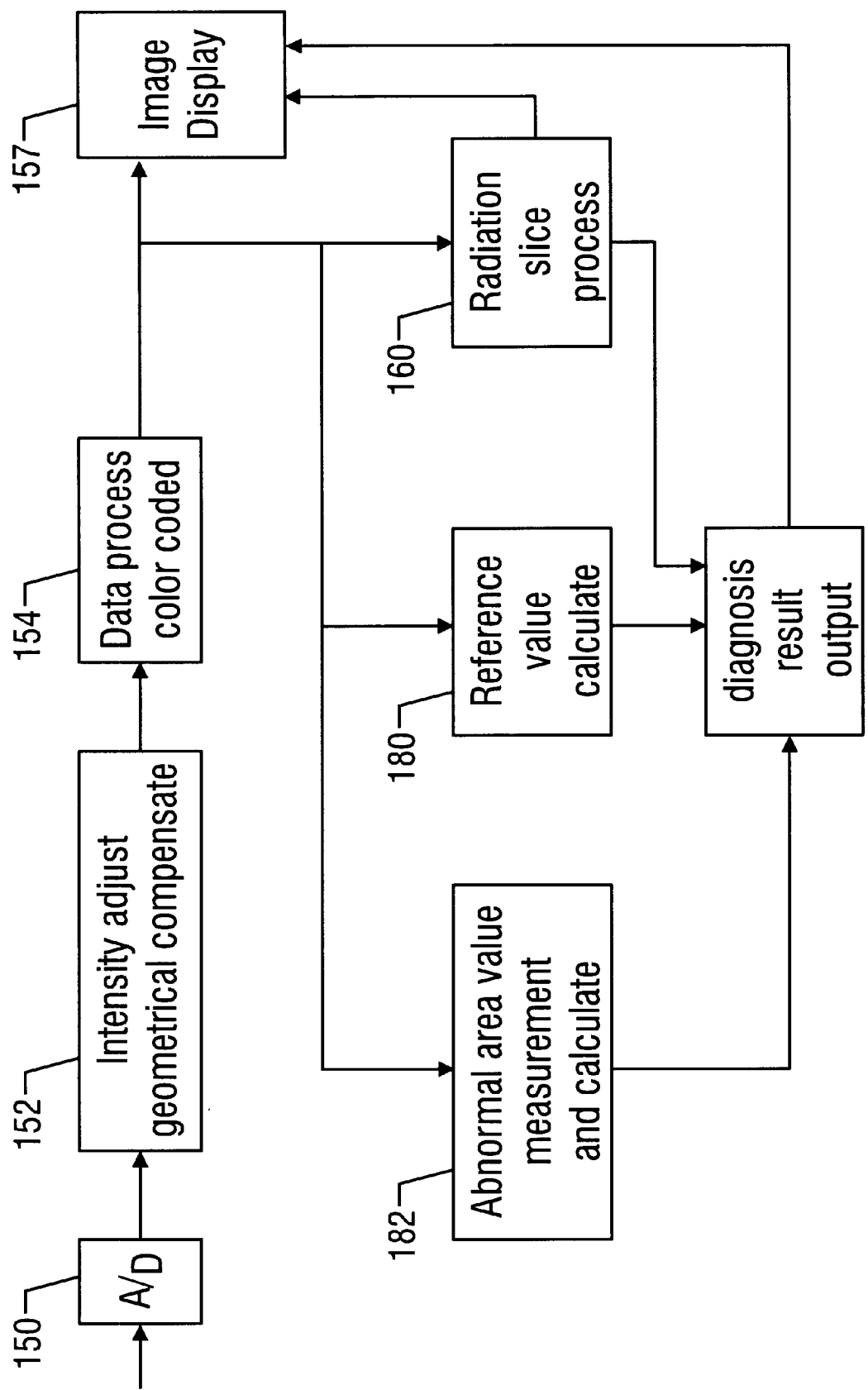
FIG. 14 is a functional flow diagram illustrating operation of control software for the imaging system of FIG. 6.

The digitized output from ADC 86 is then provided to computer 52 for processing in accordance with the present invention. FIG. 14 is a functional flow diagram illustrating the processing operations.

Block 150 in FIG. 14 represents the analog-to-digital conversion operation performed by ADC 86. The digital output of ADC 86 is then processed for intensity adjustment and geometric compensation, as represented by block 152 in FIG. 154. Intensity adjustment refers essentially to the normalization of the digital data, to compensate for the variance in base levels of intensity thermal radiation from patient to patient. That is, each patient will radiate thermal energy over a range or spectrum of intensities whose upper and lower limits will likely be different than other patients. Intensity adjustment normalizes each patient's thermal energy spectrum to a common range. (It is to be understood that, at least for the purposes of the present disclosure, "thermal energy" and "temperature" are not precisely the same thing, although sometimes "temperature" is used herein as a shorthand reference to "thermal energy." In particular, after the intensity adjustment step of block 152, a given "thermal energy" level, when quantified, may not correspond to the same "temperature" (measured, for example, in degrees centigrade), for two different patients. In any event, "thermal energy" will be reflected by the intensity of thermal or infrared radiation, which is fundamentally what the present invention concerns.)

With continued reference to FIG. 14, the geometric compensation processing performed in block 152 refers to spatial processing of the digitized thermal data to compensate for the essentially sinusoidal modulation of the scanned data arising from the oscillatory nature of the horizontal and vertical optics systems 126 and 130. It is believed that those of ordinary skill in the art will appreciate that, as optics systems 126 and 130 oscillate back and forth to accomplish the scanning of a scanning area, the effective geometric relationship between scanned points may be modulated in, for example, a sinusoidal or pseudo-sinusoidal manner, and that a compensatory manipulation of the data may be necessary to establish the true geometric relationship between adjacent scanned points in the scanning area.

Figure 15:
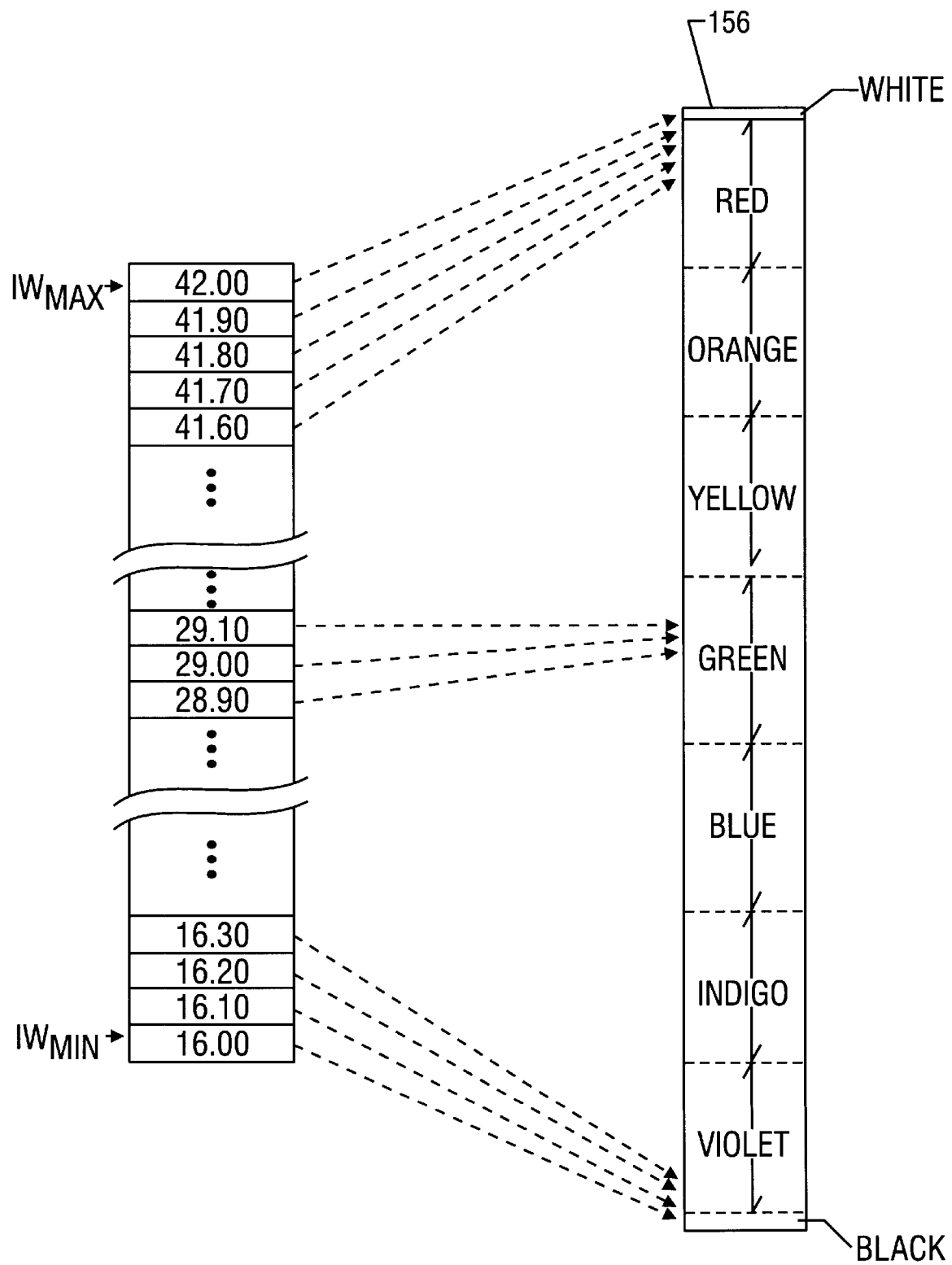
FIG. 15 is a diagram illustrating color mapping of thermal intensity data generated by the imaging system of FIG. 6.

After processing in block 152, the processed data is then subjected to color mapping, in block 154. In the presently disclosed embodiment of the invention, color mapping refers to the assignment or mapping of color values to each thermal intensity increment within the overall thermal intensity spectrum of the scanned area. This color mapping or coding operation in accordance with the presently disclosed embodiment of the invention can perhaps be best understood with reference to FIG. 15. For the purposes of FIG. 15, it is assumed that the range or spectrum of thermal intensity values in the scanned area, after intensity adjustment in block 152 (referred to herein as the "input window"), referred to with reference number 155 in FIG. 15, ranges between 13.90 and 39.50 (again, units for these values are more or less arbitrary, and do not necessarily correspond with "temperature" in degrees centigrade). (As a matter of nomenclature, the maximum radiation intensity value in the input window will be referred to as $IW_{MAX}$ and the minimum radiation intensity level in the input window will be referred to as $IW_{MIN}$. In FIG. 15, $IW_{MAX}$ is 42.00 and $IW_{MIN}$ is 16.00).

FIG. 15 shows a color spectrum 156 which ranges from white (at the top, in FIG. 15) to black (at the bottom), with red, orange, yellow, green, blue, indigo, and violet regions in between. For the purposes of FIG. 15, it is to be understood that each of the color regions (red, orange, yellow, etc.) is not a single color, but rather a range of colors, such that there is no distinct division between any two regions (as the black-and-white representation in FIG. 15 might otherwise suggest). That is, spectrum 156 is a conventional color spectrum which gradually transitions along the colors of the spectrum of visible colors. Numerically, however, the entire spectrum 156 can be represented by a range of discrete color values, for example, 256 color values ranging from 0 to 255.

As shown in FIG. 15, one distinctive region or color value of spectrum 156 (white in the disclosed embodiment), is preferably reserved for assignment to the highest intensity in the input window 155, $IW_{MAX}$=39.50 in the present example. Successively lower increments of the input window are assigned to correspondingly successively lower locations in the red region, then the orange region, the yellow region, etc., with the lowest increment of the input window, $IW_{MIN}$=13.90 in the present example, being assigned or mapped to the bottom of color spectrum 156. In other words, the process of "mapping" input window 155 to spectrum 156 involves mapping $IW_{MAX}$ to the highest color value in spectrum 156, mapping $IW_{MIN}$ to the lowest color value in spectrum 156, and mapping input window values between $IW_{MAX}$ and $IW_{MIN}$ evenly to the color spectrum values between the highest and lowest.

In the presently disclosed embodiment of the invention, spectrum 156 is divided into 256 distinct color values 0–255, such that, for example, the highest intensity value $IW_{MAX}$ is assigned color value 255 and the lowest intensity value $IW_{MIN}$ is assigned color value 0. Those of ordinary skill in the art will appreciate, therefore, that depending upon the magnitude of the thermal intensity input window 155, some intensity values may be assigned to the same color value (if the number of increments of intensity in the input window 155 exceeds 256) or, conversely, some color values may not have intensity values assigned to them (if the number of increments of intensity in the input window 155 is less than 256). In the illustrative example of FIG. 15, however, the number of increments in the input window 155 is advantageously selected to be 256, such that there is a one-to-one correspondence between the number of intensity increments and the number of color values in spectrum 156. This is, however, not believed to be essential for the purposes of practicing the present invention.

(Some more or less arbitrary assumptions are made for the purposes of the illustrative embodiment of FIG. 15 which are not critical for the purposes of the present invention. For example, it is assumed in FIG. 15 that the input window of thermal intensity values is divided into increments of tenths of a unit; also, the order of succession of colors in spectrum 156 is also more or less arbitrary. It is to be understood that such assumptions can be varied for the purposes of practicing the present invention. For example, it may be desired to increase or decrease the size of successive increments in the thermal intensity input window 155 (e.g., to halves of units, or hundredths of units), and/or to re-order the color regions of spectrum 156. It is contemplated that the sizing or increments in the thermal intensity input window may be controllable on a dynamic basis by the user of the system. That is, it is contemplated that the control software for the system may include options for adjusting the sizing or increment (resolution) of the input window.

After color mapping of the thermal intensity input window 155 to spectrum 156, the thermal data may at this stage be displayed in accordance with such mapping; that is, the mapping of window 155 to spectrum 156 determines what color value will be assigned to each data value in the thermal data. This displaying is represented by block 157 in FIG. 14, and such display enables the clinician to view a thermographic image of the scanned area. An example of such a thermographic image as it might appear on display 62 (see FIG. 6) is designated with reference numeral 158 in the color image of FIG. 16. Such a thermographic 158 image is believed to differ from conventional thermographic images in several respects, as a result, for example, of the filtering and modulating of the thermal radiation as it is scanned and of the intensity adjustment processing discussed above.

However, in accordance with an important aspect of the present invention, additional processing of thermal intensity input data is performed to achieve an even further enhanced diagnostic functionality.

As represented by block 160 in FIG. 14, the color-coded thermal intensity input data from processing block 154 is next subjected, in accordance with one aspect of the present invention, to what is referred to herein as a thermal radiation "slice process."

Figure 17:
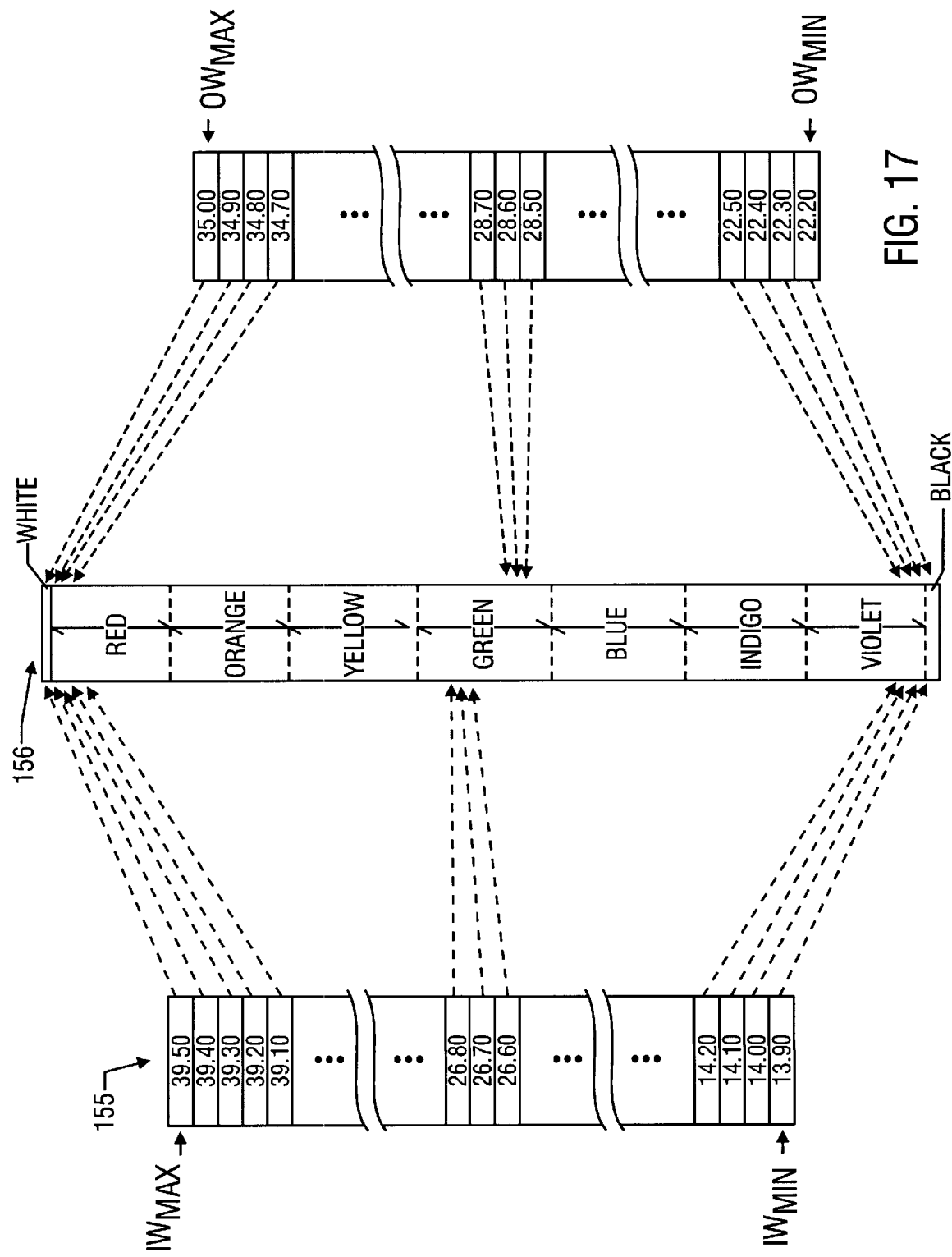
FIG. 17 is a diagram illustrating color mapping of thermal data before and after computer processing in the imaging system of FIG. 6.

The first stage of the slice process involves defining an output intensity window comprising a range of intensity values preferably smaller than the range of intensity values in the input intensity window 155. Then, each increment in the output intensity window is mapped to a color value in color spectrum 156. FIG. 17 illustrates this process. In the illustrative embodiment of the invention, a scaling factor of ½ is used to define the output intensity window, which is designated with reference numeral 162 in FIG. 17. That is, whereas the input intensity window 155 has a range of 25.60 intensity increments (that is, $IW_{MAX} - IW_{MIN} = 25.60$), the output intensity window is selected to have one-half of that range, or 12.80 intensity increments (35.00−22.20=12.80). (Again, as a matter of nomenclature, the range of the output window will be deemed to range between a maximum value $OW_{MAX}$ and a minimum value $OW_{MIN}$.)

Stated more mathematically, the process of defining output intensity window 162 involves selecting $OW_{MAX}$ and $OW_{MIN}$ such that $OW_{MIN} \geq IW_{MIN}$, $OW_{MAX} \leq IW_{MAX}$ and $(OW_{MAX} - OW_{MIN}) < (IW_{MAX} - IW_{MIN})$. For a scaling factor of ½, $(OW_{MAX} - OW_{MIN}) = 1/2(IW_{MAX} - IW_{MIN})$.

It is to be understood that the scaling factor for defining the output intensity window may be selected to be greater or less than ½, which is used in FIG. 17 merely as an illustrative example. In the preferred embodiment, in fact, the scaling factor for defining the output intensity window is among the operational processing parameters which can be adjusted up or down on a dynamic basis, as will be hereinafter described in further detail.

Having selected the output intensity scaling factor, the output intensity window 162 can then be mapped to spectrum 156, as depicted in FIG. 17. In FIG. 17, the 12.80 increment range of output intensity window 162 ranges between intensity values $OW_{MAX} = 35.00$ and $OW_{MIN} = 22.20$. However, in accordance with one aspect of the present invention, since output intensity window 162 is smaller than input intensity window 155, it is possible for output intensity window 162 to fall in any 12.80 increment range of the 25.60 increment range of the input intensity window 155. That is, it is possible to "slide" or adjust the output intensity window 162 up and down within the input intensity window 155.

Figure 18:
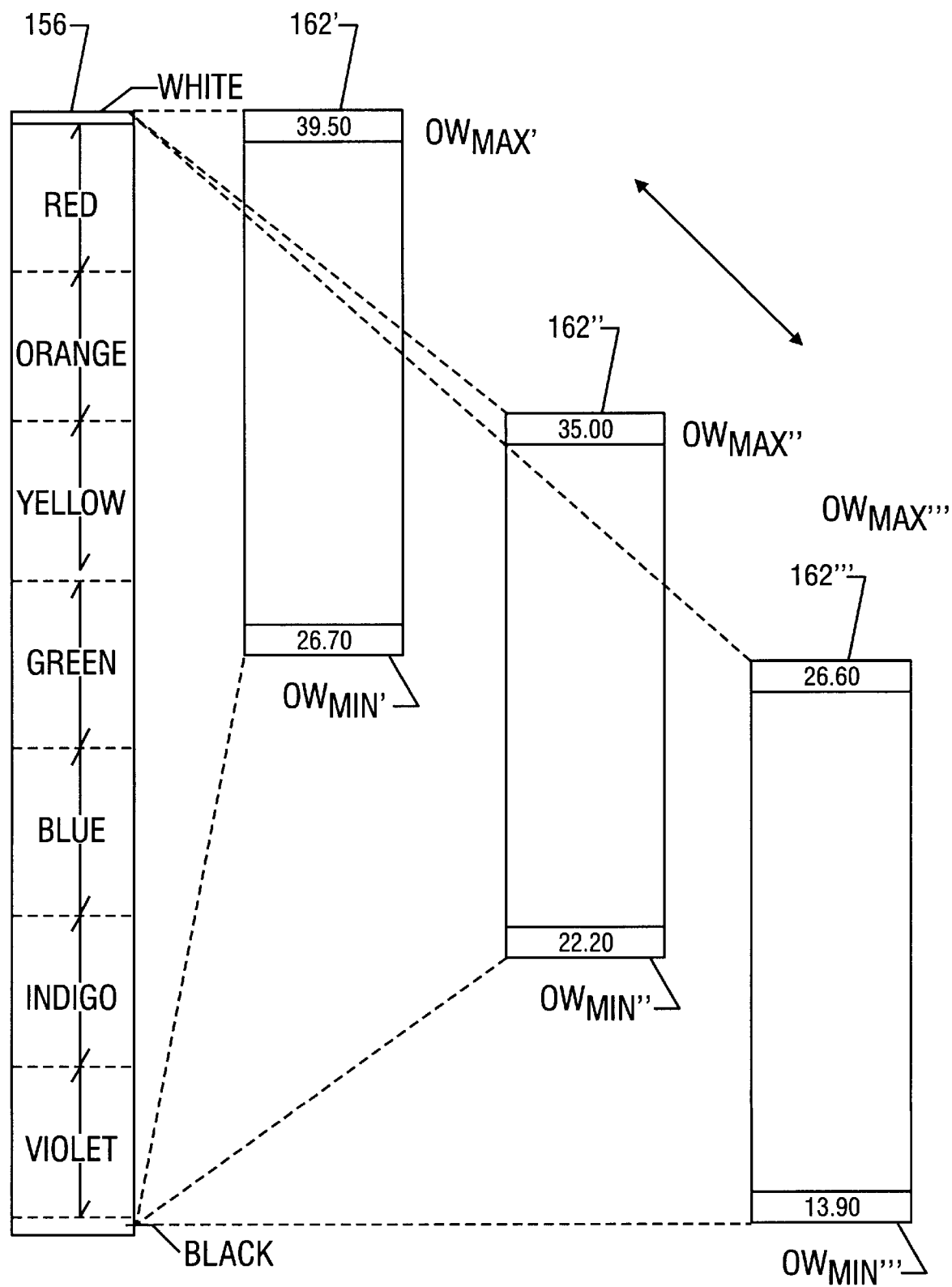
FIG. 18 is a diagram illustrating a thermal radiation slice operation performed by the imaging system of FIG. 6 on thermal intensity data.

The sliding adjustment of output intensity window 162 illustrated in FIG. 18, which shows output intensity window 162 as it is adjusted from a first position (162') in which it is mapped to an intensity range between $OW_{MIN}' = 26.70$ and $OW_{MAX}' = 39.50$ to a second position (162") in which it mapped an intermediate intensity range between $OW_{MIN}'' = 22.20$ and $OW_{MAX}'' = 35.00$, to a third position (162''') in which it is mapped to an intensity range between $OW_{MIN}''' = 13.90$ and $OW_{MAX}''' = 26.60$. In each case, while the intensity range to which the output window 162 is mapped is adjusted, the output window 162 continues to be mapped to the entire color spectrum 156. Thus, for output window 162', intensity value $OW_{MAX}' = 39.50$ is mapped to the highest color value in spectrum 156 (the contrasting white color, in the presently disclosed embodiment), while intensity value $OW_{MIN}' = 26.70$ is mapped to the lowest value in spectrum 156. When the output window 162 is adjusted down (reference numeral 162"), intensity value $OW_{MAX}'' = 35.00$ is mapped to the highest color value and $OW_{MIN}'' = 22.20$ is mapped to the lowest. Finally, at the lowest adjustment (reference numeral 162'''), intensity value $OW_{MAX}''' = 26.60$ is mapped to the highest color code and intensity value $OW_{MIN}''' = 13.90$ is mapped to the lowest.

Those of ordinary skill in the art will appreciate that the adjustment of the output intensity window 162 as described with reference to FIG. 18 is readily accomplished by processor 52 under control of user commands. For example, as in the presently disclosed embodiment, the output intensity window can be continuously adjusted up or down as illustrated in FIG. 18 in response to depression of "up arrow" and "down arrow" keys associated with computer 52.

The adjustment of the output intensity window mapping as illustrated in FIG. 18 is referred to as a "slicing" function due to a visual effect that is produced as a result of the adjustment, as will be hereinafter described in further detail.

Once the output window 162 has been mapped to spectrum 156 as just described, the "slicing" image can then be displayed. That is, by defining the output intensity window mapping, a new assignment of color values to data in the input thermal data can be performed in accordance with that mapping. By "in accordance with the mapping," it is meant that each input data value is assigned the color to which that value in output window 162 is mapped. (In one embodiment, data values in the thermal data which are below the output window 162 (i.e., data values below $OW_{MIN}$) are assigned the lowest color value, while data values in the thermal data which are above the output window 162 (i.e., data values above $OW_{MAX}$).)

Figure 16:
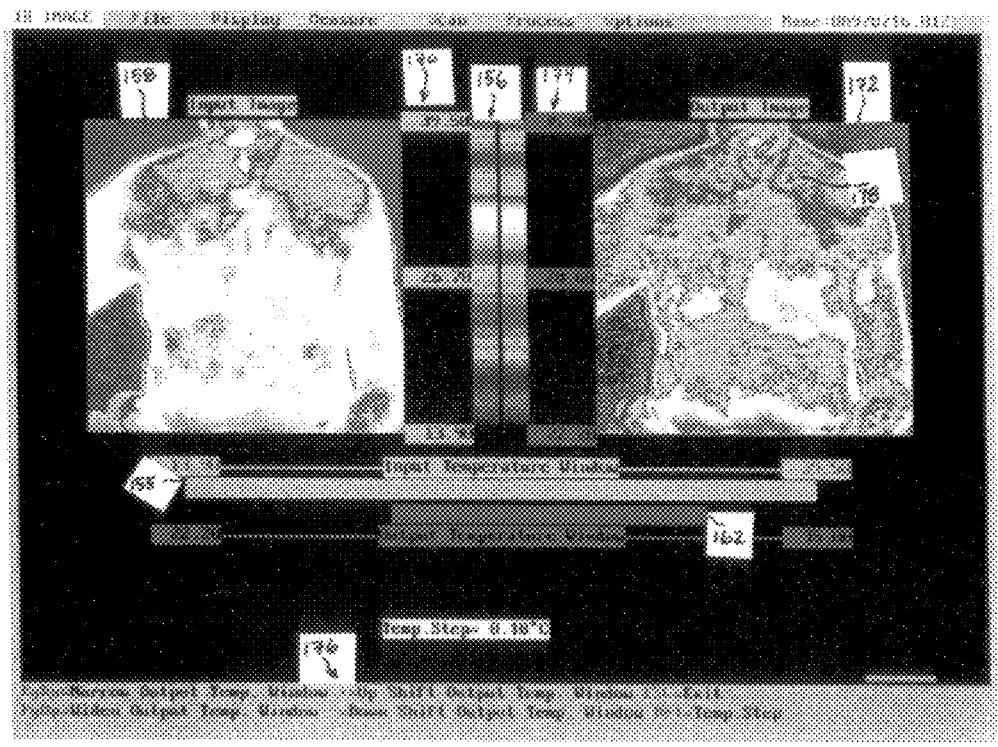
FIG. 16 is a color image of a display screen from the imaging system of FIG. 6 during a scanning procedure.

FIG. 16 is a color illustration of the image presented to the operator of the system 50 in accordance with the presently disclosed embodiment of the invention, as the image would appear on display unit 62, which may be a conventional VGA or SVGA computer monitor or the like, or as it would appear in hardcopy form from printer 64.

As previously noted, the image of FIG. 16 includes a display 158 of the input thermal intensity data, i.e., the scanned thermal image prior to being subjected to the slice operation described above with reference to FIGS. 17 and 18. Index labels designated generally with reference numeral 170 along the right-hand side of input image 158 indicate that the input thermal data from the scan image ranges between 13.90 and 39.50. Spectrum 156 also appears in the display image of FIG. 16.

An output image 172 is disposed generally on the right-hand side of the image of FIG. 16. Output image 172 is generated by subjecting the input thermal data used to generate the input image 158 to the thermal radiation slice processing (block 160 in FIG. 14). Index labels designated generally with reference numeral 174, disposed to the left of output image 172, indicate that the output image 172 spans a thermal intensity range between $OW_{MIN} = 22.20$ and $OW_{MAX} = 35.00$ as depicted in FIG. 16.

In accordance with an important aspect of the invention, and as previously described, the system 50 allows the operator to adjust the output image window up and down. A menu 176 along the bottom of the image of FIG. 16 indicates that in the presently disclosed embodiment, the output image adjustment is accomplished by depressing the "+" or "−" keys associated with computer 52. In the image of FIG. 16, the input intensity window is represented by bar 155, and can be seen to extend over a range between $IW_{MIN}$=13.90 and $IW_{MAX}$=39.50 (25.60 units), while the output intensity window, represented by bar 162, extends over a range between $OW_{MIN}$=22.20 and $OW_{MAX}$=35.00 (12.80 units, or an output window scaling factor of ½, as previously discussed). Menu 176 further indicates that the "PgDn" and "PgUp" keys associated with computer 52 can be used to narrow or widen the output image intensity window, i.e, to decrease or increase the output window scaling factor.

Use of the thermal imaging system in accordance with the presently disclosed embodiment of the invention will now be described. First, the patient is placed in scanning bed 54 (see FIG. 6), and the operator positions the patient appropriately using the control on operator console 70, so that the anatomical area of interest is positioned within the scanning field.

Next, the thermal scan is performed, to derive a 256×256 matrix of thermal data to processed as described above. At this stage, the input image 158 and an output image 172 may be displayed on display 62.

As previously discussed, the present invention is believed to be advantageously applicable to detection, identification and/or diagnosis of certain disorders, such as cancer, that are responsible for certain characteristic internal metabolic (i.e., thermal) activity, where such internal metabolic activity has not heretofore been readily or reliably detectable using conventional thermographic imaging systems such as have been shown in the prior art. The thermal radiation "slicing" processing in accordance with the present invention, however, enables such internal metabolic activity to be more readily detected, identified and perceived. This is accomplished by identifying certain characteristic variations in the images resulting from performing the slicing operation on scanning data one or more times. That is, it has been found that there are certain types of variations in the image which, when detected, can provide useful information about underlying internal metabolic activity.

After a thermal scan has been taken of an anatomic area of interest, the operator of the thermal system in accordance with the presently disclosed embodiment of the invention adjusts the output image 172 such that, in the area of interest, i.e., in an area in which an internal thermal body, such as a tumor or the like, is suspected of existing, the color value representing the highest thermal intensity value is mapped to the most thermally intense location in the area of interest. Visually, this is accomplished by adjusting or shifting the output window up or down until a small white area— initially merely a dot—appears in the area of interest. (Recall that the highest color value in the spectrum 156 is white, purposefully in contrast to the color values immediately below, red in the presently disclosed embodiment of the invention. This purposeful contrast enables the most thermally intense location(s) in an image to be readily observed).

In FIG. 16, the output window has been shifted by the operator so that such a white dot, designated with reference numeral 178 in FIG. 16, has appeared in the patient's left clavicle region. To better illustrate the diagnostic process in accordance with the presently disclosed embodiment of the invention, dot 178 is reproduced in FIG. 19.

Next, the physician shifts the input temperature window up incrementally. In the embodiment of FIG. 16, a legend 180 indicates the increment for units in the input and output intensity windows is 0.10, so that shifting output window 162 up one increment will cause it to span an intensity range from $OW_{MIN}$=22.30 to $OW_{MAX}$=35.10, shifting it up two increments will cause window 162 to span a range $OW_{MIN}$= 22.40 to $OW_{MAX}$=35.20, and so on.

Because of the internal thermal radiation behavior discussed above with reference to FIGS. 1–5, an therefore in accordance with an important aspect of the present invention, it has been clinically found by the inventors that when a metabolically active body (e.g., a cancer) is present within a patient's body, as the output window 162 is shifted up as described herein, the region 178 mapped to the color value at the highest end of spectrum 156 will tend to increase in size in a more or less consistent and uniform manner. The point at which such sudden, non-incremental or non-uniform transition occurs can, it is believed, be correlated with the depth of the internal metabolically active region underlying region 178.

Figure 19:
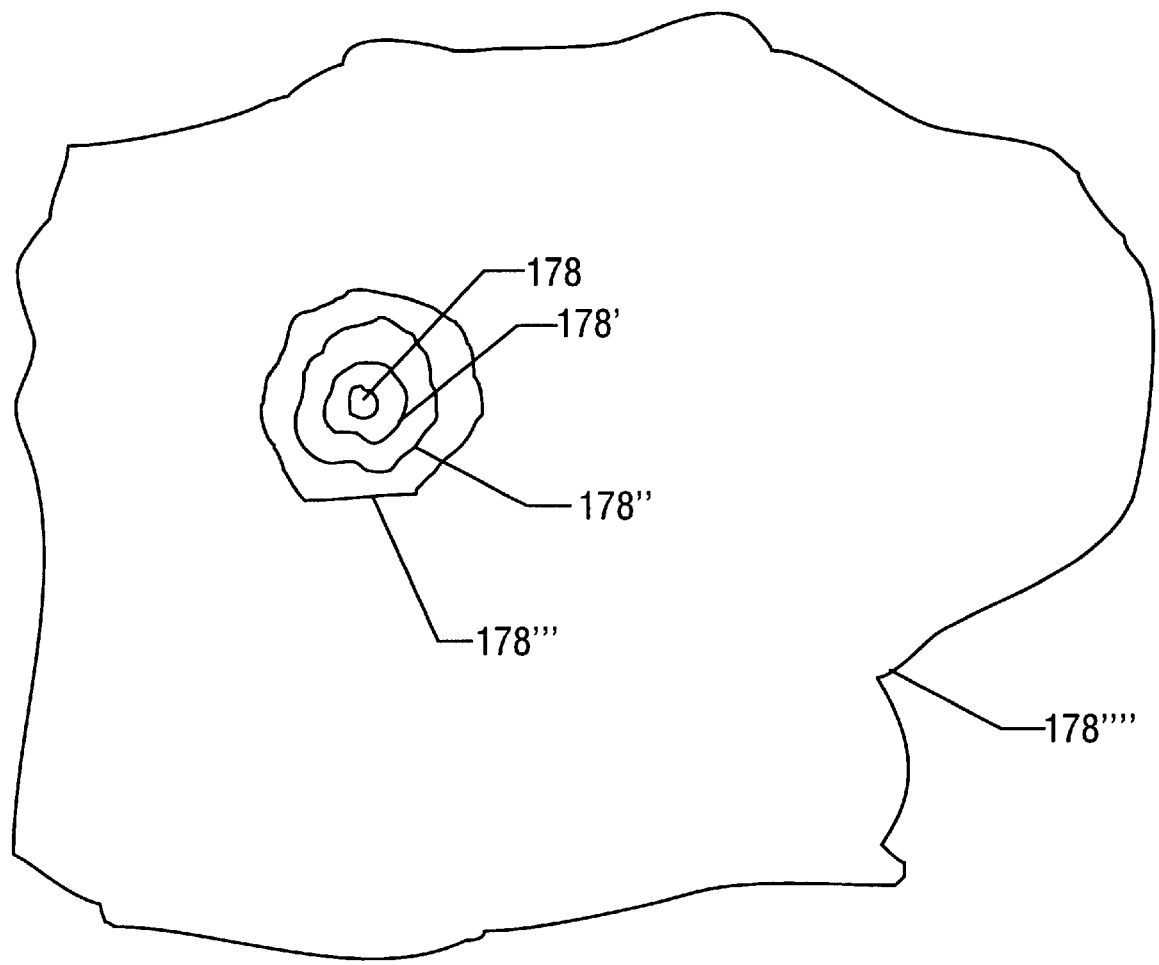
FIG. 19 is a diagram illustrating the visual display resulting from performing the thermal radiation slice operation of FIG. 18 on thermal intensity data associated with a suspected anatomical region.

Referring to FIG. 19, for example, recall that region 178 represented the small white dot in the scanning area of interest. Assuming that dot 178 is present due to an internal metabolically active body (e.g., a tumor) when output window 162 is shifted up one increment, region 178 will enlarge slightly, appearing as a generally well-defined area as represented by reference numeral 178' in FIG. 20. Shifting the output window 162 up one further increment will cause region 178 to enlarge still further, but still in a more or less bounded fashion, so as to appear as designated with reference numeral 178", and shifting window 162 still another increment will cause region 178 to enlarge to appear as designated with reference numeral 178'". This gradual and more or less uniform enlarging of region 178 can be observed by the operator on display 62.

It has been found that upon further incremental shifting of output window 162, a suspected region which initially appeared as a dot 178 in FIG. 19 and which, upon shifting the output window incrementally, tended to incrementally enlarge, will at some point abruptly enlarge in an amorphous and discontinuous manner as output window 162 is incrementally shifted. That is, as output window 162 is incremented, causing gradual and smooth enlargement of region 178, the region will eventually suddenly enlarge, for example, from the region designated with reference numeral 178'" in FIG. 20 to that designated 178'" with only one (or perhaps two) incremental shifts in output intensity window 162. Such abrupt, non-incremental enlarging is readily distinguished from the gradual, incremental enlarging that region 178 undergoes at first, and can be readily observed by the operator.

While in the presently disclosed embodiment of the invention it is considered that an operator will be present to observe the sudden, discontinuous expansion of region 178, thus giving insight into the depth of the underlying metabolic activity reflected by region 178, it is also contemplated that known or to-be-developed computational algorithms can be applied to enable certain characteristic changes or variations in the images, such as the first incremental continuous and later discontinuous expansions (i.e., discontinuities) discussed above to be detected by means of computer analysis, i.e., without the intervention of human observation, or at least without the full reliance upon human observation.

In accordance with another important aspect of the present invention, the point at which the non-incremental and discontinuous transition of region 178 (i.e., the transition from region 178'" to region 178"") occurs can be correlated to the depth of the internal metabolic body that the thermal region 178 reflects. That is, the magnitude of the overall shift in output intensity window 162 which causes region 178 to gradually enlarge from its appearance designated with numeral 178 to its appearance designated with reference numeral 178"" can be correlated to the depth of the internal metabolic body. This correlation can take into account the known relative thermal conductivities of various types of body tissue (fatty tissue, muscle, bone, etc.), as previously discussed.

As noted above, one advantageous aspect of the imaging system in accordance with the present invention is its ability to generate accurate and meaningful results in spite of variations in thermal radiation intensity ("temperature") from patient to patient. This capability arises in part from a reference value calculation function of the processing software represented by the flow diagram of FIG. 14. The reference value calculation, represented by block 180 in FIG. 14, operates in one embodiment as follows: after a thermally radiating object in an anatomical area of interest has been identified, for example as discussed above with reference to FIG. 19, the system operator uses the mouse or other cursor control device associated with computer system 52, to identify a reference region at some other anatomical area appearing in the image likely to have the same thermal characteristics under normal circumstances. For example, since the region 178 identified in the output image (FIGS. 16 and 19) in the illustrative example was located on the patient's left shoulder/clavicle area, the operator may designate an area in the patient's right shoulder/clavicle area as the reference.

Block 180 represents a function of the software executed by processor 52 wherein an average thermal radiation intensity value is calculated for the reference area identified by the operator. This value may then be used as a reference against which the thermal intensity of the suspected region (spot 178) can be compared in order to ascertain the relative intensity thereof. Block 182 in FIG. 14 represents the operation of calculating the thermal intensity associated with the suspected area. As with the derivation of the reference value, the operation represented by block 182 in one embodiment involves the operator identifying the boundaries of the suspected area (for example, by using the mouse or cursor control device associated with computer 52).

As applied to diagnosis of cancerous conditions, for example, a threshold in the difference between the thermal radiation intensity of the suspected area (spot 178) and the reference value can be established, such that suspected areas which exceed this threshold are considered indicative of a cancerous condition.

It is to be noted that, in accordance with one aspect of the present invention, by assessing the thermal intensity of a suspected area by comparison to a reference value derived from the patient (as opposed to a reference value taken from a population average, for example), the effects of patient-to-patient variations in base levels of thermal radiation are minimized.

Figure 20:
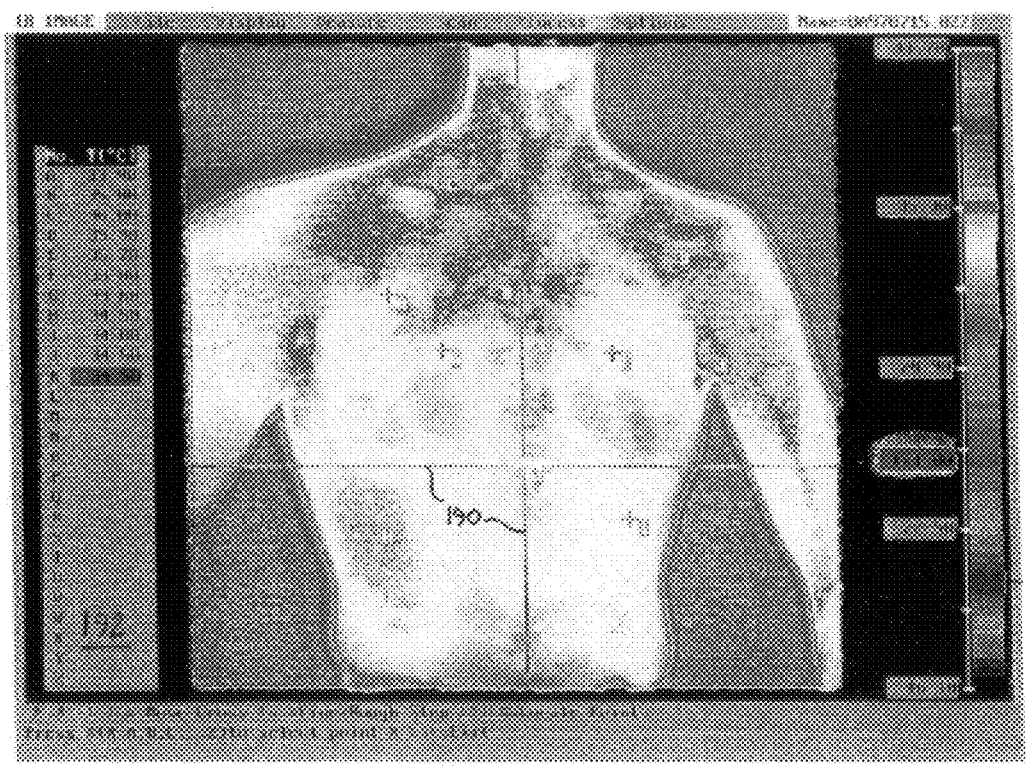
FIG. 20 is a color image of a display screen from the imaging system of FIG. 6 during a temperature measurement operation.

Referring now to FIG. 20, there is shown still another functional capability of the system 50 in accordance with the presently disclosed embodiment of the invention. In particular, illustrated in FIG. 20 is a temperature-measurement function whereby the operator can identify selected locations in a thermal image and cause the temperature at those locations to be displayed. Using a mouse or other cursor control device associated with computer 52, the operator causes a set of cross-hairs 190 to move about the image. At desired locations, the operator then depresses the mouse button or another key associated with computer 52. This causes the location to be labeled (labels A-K appear in FIG. 20), and in a table 192 to the left of the image, the respective temperatures corresponding to the selected points are listed. This function may be advantageously employed to identify areas of high thermal radiation, suggesting that a suspicious internal thermal body is present in those areas and indicating, therefore, that the thermal "slicing" operation should be performed with data in the area to further assess the condition.

From the foregoing detailed description of a specific embodiment of the invention, it should be apparent that a method and apparatus for thermal radiation imaging has been disclosed. In accordance with a significant aspect of the invention, the method and corresponding apparatus enables thermal radiation data to be processed in such a manner so as to facilitate generation of images reflecting internal thermal conditions, i.e., thermal conditions inside a human body.

Although a specific embodiment of the present invention has been disclosed herein in some detail, this has been done solely for the purposes of illustrating various aspects of the present invention, and is not intended to be limiting with respect to the scope of the invention. It is to be understood that various substitutions, alterations and modifications may be made to the invention as disclosed, including but not limited to those specifically discussed herein, without departing from the spirit and scope of the invention as defined in the appended claims, which follow.

What is claimed is:

1. An imaging system, comprising:

a scanning subsystem for generating digital data corresponding to intensity levels of infrared radiation from a scanned area of a patient's body;

a processor, coupled to said scanning subsystem to receive said digital data, for processing said data to generate image data reflecting metabolic activity internal to the patient's body beneath the scanned surface areas;

a display system for generating a display corresponding to said image data;

a control system, coupled to said processor, said display system, and said scanning subsystem, for facilitating user control of said imaging system;

wherein said processor assigns color values from a predetermined range within a spectrum of color values to each unit of said digital data, such that different infrared radiation intensity levels are assigned different color values;

and wherein said color values comprise said image data, such that when said imaging system generates a display corresponding to said image data, different colors on said display correspond to different radiation levels in said scanned area;

and wherein said digital data lies within an input window of intensity values, said input window having a minimum $IW_{MIN}$ and a maximum $IW_{MAX}$;

and wherein said processor assigns said data values to color values by (a) defining in said input window an output window of data values between a maximum output data value $OW_{MAX}$ and a minimum output data value $OW_{MIN}$, where $OW_{MAX}$ is less than or equal to $IW_{MAX}$, $OW_{MIN}$ is greater than or equal to $IW_{MIN}$, and said output intensity window is smaller than said input intensity window;

(b) mapping said output intensity window of color values to said spectrum of color values such that $OW_{MAX}$ is mapped to a highest color value in said spectrum of color values and $OW_{MIN}$ and is mapped to a lowest color value in said spectrum of color values, with all data values between $OW_{MAX}$ and $OW_{MIN}$ being evenly mapped to color values between said highest and lowest color values in said color spectrum;

(c) assigning color values to said data values in accordance with said mapping in step (b);

and wherein said control system is adapted to enable a user to dynamically adjust $OW_{MAX}$ and $OW_{MIN}$ such that sub-surface metabolic activity may be observed on said display.

2. A method of radiation imaging, comprising:

(a) scanning a scanning area to obtain digital data values corresponding to levels of radiation intensity at a plurality of points within said scanned area, said digital data values each having a value within an input window of data values having a minimum $IW_{MIN}$ and a maximum $IW_{MAX}$;

(b) assigning a color value within a spectrum of color values to each digital data value, to generate image data;

(c) displaying said image data on a display;

wherein said step (b) of assigning a color value to each digital data value comprises:

(d) defining within said input window an output intensity window of data values between a maximum output data value $OW_{MAX}$ and a minimum output data value $OW_{MIN}$, where $OW_{MAX}$ is less or equal to $IW_{MAX}$, is greater than or equal to $IW_{MIN}$, and said output intensity window is smaller than said input intensity window;

(e) mapping said output intensity window of color values to said spectrum of color values such that $OW_{MAX}$ is mapped to a highest color value in said spectrum of color values and $OW_{MIN}$ and is mapped to a lowest color value in said spectrum of color values, with all data values between $OW_{MAX}$ and $OW_{MIN}$ being substantially evenly mapped to color values between said highest and lowest color values in said color spectrum;

(f) assigning color values to said data values in accordance with said mapping in step (e) and (g) dynamically adjusting $OW_{MAX}$ and $OW_{MIN}$ such that sub-surface metabolic activity may be observed on said display.

3. A method in accordance with claim 2, wherein said steps (b) through (g) are performed by a computer.

4. A method of detecting internal metabolic activity in a patient, comprising:

(a) scanning a scanning area on said patient's body to obtain digital data values corresponding to levels of radiation intensity at a plurality of points within said scanned area;

(b) assigning a color value within a spectrum of color values to each digital data value, to generate image data, said digital data values each having a value within an input window of data values having a minimum $IW_{MIN}$ and a maximum $IW_{MAX}$; and (c) displaying said image data;

wherein said step (b) of assigning a color value to each digital data value comprises:

(d) defining within said input window an output intensity window of data values between a maximum output data value $OW_{MAX}$ and a minimum output data value $OW_{MIN}$, where $OW_{MAX}$ is less than or equal to $IW_{MAX}$, $OW_{MIN}$ is greater than or equal to $IW_{MIN}$, and said output intensity window is smaller than said input intensity window;

(e) mapping said output intensity window of color values to said spectrum of color values such that $OW_{MAX}$ is mapped to a highest color value in said spectrum of color values and $OW_{MIN}$ and is mapped to a lowest color value in said spectrum of color values, with all data values between $OW_{MAX}$ and $OW_{MIN}$ being substantially evenly mapped to color values between said highest and lowest color values in said color spectrum;

(f) assigning color values to said data values in accordance with said mapping in step (e) and (g) generating an adjusted image by dynamically adjusting $OW_{MAX}$ and $OW_{MIN}$ such that sub-surface metabolic activity may be observed on said display.

5. A method in accordance with claim 4, wherein said steps (b) through (g) are performed by a computer.

6. A method in accordance with claim 4, further comprising:

(h) detecting at least one predetermined type of variation in said adjusted image as compared with said image displayed in step (c).

7. A method in accordance with claim 6, wherein said step of detecting is performed by a computer.

8. A method of manipulating image data comprising a plurality of data values each corresponding to elements of an image, wherein said data values each having a value within an input window of data values having a minimum $IW_{MIN}$ and a maximum $IW_{MAX}$, comprising:

(a) defining within said input window an output intensity window of data values between a maximum output data value $OW_{MAX}$ and a minimum output data value $OW_{MIN}$, where $OW_{MAX}$ is less than or equal to $IW_{MAX}$, $OW_{MIN}$ is greater than or equal to $IW_{MIN}$, and said output intensity window is smaller than said input intensity window;

(b) mapping said output intensity window of color values to a spectrum of color values such that $OW_{MAX}$ is mapped to a highest color value in said spectrum of color values and $OW_{MIN}$ and is mapped to a lowest color value in said spectrum of color values, with all data values between $OW_{MAX}$ and $OW_{MIN}$ being substantially evenly mapped to color values between said highest and lowest color values in said color spectrum;

(c) assigning color values to said data values in accordance with said mapping in step (e); and (d) dynamically adjusting $OW_{MAX}$ and $OW_{MIN}$.

9. A method in accordance with claim 8, wherein said image data is obtained by optically scanning an area to be imaged.

10. A method in accordance with claim 9, wherein said area to be imaged is an area of a human body.

\* \* \* \* \*

UNITED STATES PATENT AND TRADEMARK OFFICE
CERTIFICATE OF CORRECTION

PATENT NO. : 6,023,637
DATED : February 8, 2000
INVENTOR(S) : Zhong Qi Liu and Chen Wang Page 1 of 1

It is certified that error appears in the above-identified patent and that said Letters Patent is hereby corrected as shown below:

Column 20, claim 1,
Line 39, should read -- area -- instead of "areas".

Column 21, claim 2,
Line 33, should read -- or equal to $IW_{MAX}$, $OW_{MIN}$ is --.

Signed and Sealed this

Fifth Day of February, 2002

Attest:

JAMES E. ROGAN
Attesting Officer  Director of the United States Patent and Trademark Office